US010450629B2

(12) United States Patent
Mary et al.

(10) Patent No.: US 10,450,629 B2
(45) Date of Patent: Oct. 22, 2019

(54) USE OF NOVEL COMPOUNDS FOR SELECTIVELY EXTRACTING RARE EARTHS FROM AQUEOUS SOLUTIONS INCLUDING PHOSPHORIC ACID AND ASSOCIATED EXTRACTION METHOD

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE DE MONTPELLIER, Montpellier (FR)

(72) Inventors: Fanny Mary, Valreas (FR); Guilhem Arrachart, Saint-Laurent-des-Arbes (FR); Stephane Pellet-Rostaing, Villeurbanne (FR); Antoine Leydier, Saint Etienne (FR); Veronique Dubois, Gaujac (FR)

(73) Assignees: COMMISSARIAT A L+ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/571,967

(22) PCT Filed: May 3, 2016

(86) PCT No.: PCT/EP2016/059827
§ 371 (c)(1),
(2) Date: Nov. 6, 2017

(87) PCT Pub. No.: WO2016/177695
PCT Pub. Date: Nov. 10, 2016

(65) Prior Publication Data
US 2018/0142321 A1    May 24, 2018

(30) Foreign Application Priority Data

May 7, 2015    (FR) ...................... 15 54119

(51) Int. Cl.
*C22B 3/00* (2006.01)
*C22B 3/26* (2006.01)
(Continued)

(52) U.S. Cl.
CPC .......... *C22B 3/0006* (2013.01); *C07F 9/4006* (2013.01); *C22B 3/06* (2013.01); *C22B 59/00* (2013.01); *Y02P 10/234* (2015.11)

(58) Field of Classification Search
CPC ......... C22B 3/06; C22B 3/0006; C22B 59/00; C07F 9/4006; Y02P 10/234
(Continued)

(56) References Cited

U.S. PATENT DOCUMENTS 4,461,748 A    7/1984 Sabot et al.

FOREIGN PATENT DOCUMENTS

| EP | 0 079 258 A1 | 5/1983 |
| EP | 0 284 504 A1 | 9/1988 |
| RU | 2544731 | * 3/2015 |

OTHER PUBLICATIONS

International Search Report date Jul. 21, 2016 in PCT/EP2016/059827 filed May 3, 2016.
(Continued)

*Primary Examiner* — Steven J Bos
(74) *Attorney, Agent, or Firm* — Oblon, McClelland, Maier & Neustadt, L.L.P.

(57) ABSTRACT

The invention relates to the use, as an extraction agent for extracting at least one rare earth from an aqueous phase including phosphoric acid, of at least one compound of the following general formula (I):

$$R_3 \underset{R_1}{\overset{}{\diagdown}} O \left( \underset{}{\diagdown} O \right)_n \underset{R_2}{\overset{}{\diagdown}} R_4 \quad (I)$$

where
n is an integer equal to 0, 1 or 2,
$R_1$ and $R_2$ are H or an aliphatic hydrocarbon group,
one of $R_3$ and $R_4$ has the following formula (II):

$$R_5 \underset{R_6}{\overset{O}{\underset{\|}{\diagdown}}} P \quad (II)$$

where $R_5$ and $R_6$ are a hydrocarbon, hydroxyl or alkoxyl group, and
the other one of $R_3$ and $R_4$ has one of the following formulas (II') and (III):

$$R_5' \underset{R_6'}{\overset{O}{\underset{\|}{\diagdown}}} P \quad (II')$$

(Continued)

-continued

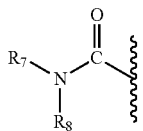

(III)

where $R_5'$ and $R_6'$ are a hydrocarbon, hydroxyl or alkoxyl group, and $R_7$ and $R_8$ are H or an aliphatic hydrocarbon group.

The invention also relates to a method for recovering at least one rare earth using said compound, as well as to specific compounds as such.

18 Claims, No Drawings

(51) Int. Cl.
  *C22B 3/06* (2006.01)
  *C22B 59/00* (2006.01)
  *C07F 9/40* (2006.01)

(58) Field of Classification Search
  USPC .......................................................... 423/21.5
  See application file for complete search history.

(56) References Cited

OTHER PUBLICATIONS

French Search Report dated Jan. 7, 2016 in FR 1554119 filed May 7, 2015.
Mudassir Iqbal et al., "Synthesis and evaluation of ligands with mixed amide and phosphonate, phosphinoxide, and phosphonothioate sites for an(III)/Ln(III) extraction," New Journal of Chemistry, vol. 36, No. 10, Jan. 2012, XP055220813, pp. 2048-2059.
A.R.P.M. Valentijn et al., "Synthesis of Pyrophosphonic Acid Analogues of Farnesyl Pyrophosphate," Tetrahedron, Elsevier Science Ltd Publishers, Amsterdam, NL, vol. 51, No. 7, Feb. 1995, XP004104839, pp. 2099-2108.
Timothy Haemers et al., "Syntehsis of β- and γ-oxa isosteres of fosmidomycin and FR900098 as antimalarial candidates," Bioorganic and Medicinal Chemistry, Pergamon, GB, vol. 16, No. 6, Oct. 2007, XP022558569, pp. 3361-3371.
Mudassir Iqbal et al., "Synthesis and evaluation of novel water-soluble ligands for the complexation of metals during the partitioning of actinides," New Journal of Chemistry, vol. 35, No. 11, Jan. 2011, pp. 2591-2600.

\* cited by examiner

USE OF NOVEL COMPOUNDS FOR SELECTIVELY EXTRACTING RARE EARTHS FROM AQUEOUS SOLUTIONS INCLUDING PHOSPHORIC ACID AND ASSOCIATED EXTRACTION METHOD

TECHNICAL FIELD

The present invention relates to the field of the extraction of rare earths from acid aqueous phases in which said rare earths are present.

It more specifically relates to the use of at least one specific compound as an extraction agent, for extracting at least one rare earth from an acid aqueous phase in which said at least one rare earth is present.

The invention also relates to a method for recovering at least one rare earth present in an acid aqueous phase, said method implementing this specific compound.

The acid aqueous phase from which the rare earth(s) may be extracted, or from which they may be recovered, is an aqueous solution comprising phosphoric acid. Such an aqueous solution may notably be a solution deriving from an acid digestion of a concentrate of ores or wastes comprising said at least one rare earth.

The present invention notably finds application in the treatment of natural ores and/or industrial wastes with a view to reusing the rare earths present therein.

The present invention finally relates to certain specific compounds of which the use is mentioned above.

PRIOR ART

Rare earths group together metals characterised by related properties, namely scandium (Sc), yttrium (Y) and all of the lanthanides, the latter corresponding to the chemical elements set out in the Mendeleev periodic table of elements which have an atomic number ranging from 57 for lanthanum (La) to 71 for lutetium (Lu).

Rare earths are generally classified into two categories: cerium earths, or light rare earths, which group together Sc, Y as well as metals ranging from lanthanum (La) to neodymium (Nd), and heavy rare earths, or the yttrium group, which group together metals ranging from promethium (Pm) to lutetium (Lu).

The related properties of the rare earths are notably linked to their electron configuration, in particular to the specificity of their 4f electron subshell which enables numerous optical transitions and confers them with specific magnetic and catalytic properties. In view of these remarkable properties, rare earths are used in numerous high-tech applications such as lasers, permanent magnets, batteries or low consumption bulbs.

Consequently, rare earths form part of so-called "technological" metals, the supply of which is strategic, but also threatened under the effect of the growth in world demand for these specific metals.

Among sources of rare earths may be cited bastnaesite hard rock deposits as well as alluvial deposits of monazite and xenotime. Besides these ores, which contain the highest concentrations of rare earths, other ores may also be cited, such as phosphate ores or apatites, which are certainly poorer in lanthanides, but the exploitation and the treatment of which could be profitable in the future. In the remainder of the present description, the ores that have been cited and which contain rare earths in greater or lesser amounts are designated by the expression "natural ores".

Since rare earths are also very widely present in technological equipment, the re-use through recycling of industrial wastes stemming from such equipment, and notably from electric and electronic equipment waste, noted "EEEW" or "3EW", represents a non-conventional and alternative source of accessing rare earths. In the remainder of the present description, these industrial wastes which contain rare earths are designated by the expression "industrial ores".

The methods currently used to recover rare earths from these natural or industrial ores consist in subjecting said ores, ground beforehand, to chemical treatments, by acid or basic reagents, to obtain a mineral concentrate.

This mineral concentrate is then subjected to a chemical digestion to enable solubilisation of the rare earths that are contained therein. This chemical digestion is conventionally carried out by means of one or more acid reagents among which nitric acid, sulphuric acid, phosphoric acid or instead hydrochloric acid.

The so-called "acid digestion solution" thereby obtained is then subjected to a hydro-metallurgical treatment based on the technique of liquid-liquid extraction, a technique which consists in bringing the aqueous phase constituted by this acid digestion solution into contact with an organic phase comprising one or more extraction agents, to obtain an extraction of the rare earths, such an extraction having to be, preferably, simultaneously efficient and selective.

Among extraction agents used industrially for the extraction of rare earths may be cited bis-(2-ethylhexyl)phosphoric acid (or HDEHP), 2-ethylhexyl-2-ethylhexylphosphonic acid (or HEHEHP) as well as tri-n-butyl phosphate (or TBP), TBP being the extraction agent the most used to date.

Apart from the fact that HDEHP enables extraction of rare earths present in a strongly acidic (pH<1) aqueous phase whereas HEHEHP enables extraction of rare earths present in an acid aqueous phase acid having a 2<pH<3, these three extraction agents HDEHP, HEHEHP and TBP are characterised by a selective extraction of heavy lanthanides corresponding to lanthanides of which the atomic number is 61 or more (up to 71).

The use of such extraction agents thus does not make it possible to extract all rare earths, but only heavy rare earths. What is more, the use of HDEHP and HEHEHP extraction agents imposes determined intervals of concentration of the acid present in the aqueous phase.

A recent publication of S. Ansari et al. ("*Chemistry of Diglycolamides: Promising Extractants for Actinide Partitioning*", Chemical Reviews, 2012, 112, 1751-1772), referenced [1] at the end of the present description, describes the use of diglycolamides (or DGA), among which N,N,N',N'-tetra-n-octyldiglycolamide (or TODGA), as compounds suitable for the extraction of lanthanides and actinides present in an aqueous phase comprising nitric acid.

However, the publication [1] reports that extraction by TODGA may lead to the formation of a third phase, which is totally unacceptable for the implementation of an extraction method at an industrial scale. To remedy the formation of this third phase, the publication [1] proposes associating TODGA with a phase modifier, in this case TBP. In such a configuration, there are thus no longer one but two extraction agents to implement. Yet, such a system with two extraction agents, which notably requires the determination of an optimal ratio thereof, is obviously more awkward to manage than a system with a single extraction agent.

In the even more recent publication of H. Narita et al. ("*Separation of Rare Earth Elements from Base Metals in Concentrated $HNO_3$, $H_2SO_4$ and HCl Solutions with Digly-* colamide", Solvent Extraction Research and Development, Japan, 2013, 20, 115-121), referenced [2], the authors describe the use of N,N'-dimethyl-N,N'-di-n-octyldiglycolamide (or MODGA) as an extraction agent of neodymium Nd(III) and of dysprosium Dy(III) present in aqueous solutions comprising, moreover, iron Fe(III), nickel Ni(II) and variable molar concentrations that are comprised between 0.1 mol/L and 7 mol/L of nitric acid, hydrochloric acid or instead sulphuric acid. According to the experimental results presented in this publication [2], the most efficient and the most selective extraction of Nd and of Dy, compared to Fe and to Ni, is obtained with aqueous solutions comprising nitric acid.

Although the extraction by diglycolamides of rare earths from acid aqueous phases is known from the publications [1] and [2], it is nevertheless observed that only the extraction from aqueous phases comprising hydrochloric acid, sulphuric acid or, more widely, nitric acid has been described.

Yet, and as illustrated in example 8 hereafter, the Inventors have observed that the extraction performances described in the publication [1], with TODGA as an extraction agent and the extraction being carried out from an aqueous phase comprising nitric acid, were not transposable to an extraction carried out from an aqueous phase comprising phosphoric acid.

It is on the basis of this observation that the Inventors set themselves the aim of providing a novel family of extraction agents which have a great affinity for all or part of the rare earths and which can, consequently, be used for extracting at least one rare earth from an acid aqueous phase in which this or these rare earths are present, said acid aqueous phase comprising, as acid, phosphoric acid and not nitric, hydrochloric or sulfuric acid.

The extraction by means of this novel family of extraction agents must be able to extract the major part of the rare earths present in the aqueous phase or, on the contrary, some of these rare earths, for example as a function of their atomic number. The extraction by means of these extraction agents must also tend to be selective with respect to elements which are also likely to be present in the acid aqueous phase but which are not rare earths.

The Inventors also set themselves the aim that this extraction can be advantageously used in an interval of phosphoric acid concentrations in the aqueous phase that is as wide as possible.

The Inventors moreover set themselves the aim that this extraction can be advantageously implemented with a single extraction agent and without a third phase forming, thereby making it possible to envisage favourably transposition of the corresponding extraction method to an industrial scale.

DESCRIPTION OF THE INVENTION

The aforementioned aims and others are attained, firstly, by the use of at least one specific compound as an extraction agent, for extracting at least one rare earth from an aqueous phase in which said at least one rare earth is present, said aqueous phase further comprising phosphoric acid.

This specific compound, the use of which is the subject of the present invention, is a compound of the following general formula (I):

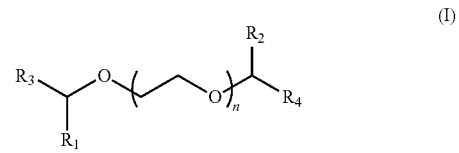

where
n is an integer equal to 0, 1 or 2,
$R_1$ and $R_2$ are, independently of each other, a hydrogen atom, a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched,
one of $R_3$ and $R_4$ has the following formula (II):

where $R_5$ and $R_6$ are, independently of each other, a $C_1$ to $C_{12}$ aliphatic hydrocarbon group, saturated or unsaturated, linear or branched, a $C_3$ to $C_8$ cyclic hydrocarbon group, saturated or unsaturated, optionally branched, a hydroxyl group —OH or an alkoxyl group —OR, with R being a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched, and
the other one of $R_3$ and $R_4$ has:
either the following formula (II'):

in which $R_5'$ and $R_6'$ are, independently of each other, a $C_1$ to $C_{12}$ aliphatic hydrocarbon group, saturated or unsaturated, linear or branched, a $C_3$ to $C_8$ cyclic hydrocarbon group, saturated or unsaturated, optionally branched, a hydroxyl group —OH or an alkoxyl group —OR', with R' being a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched,
or the following formula (III):

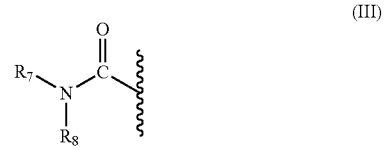

in which $R_7$ and $R_8$ are, independently of each other, a hydrogen atom, a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched.

In the foregoing and hereafter:

"$C_1$ to $C_{12}$ aliphatic hydrocarbon group, saturated or unsaturated, linear or branched", is taken to mean any alkyl, alkenyl or alkynyl group, with a linear or branched chain, which comprises in total 1 to 12 carbon atoms;

"$C_3$ to $C_8$ cyclic aliphatic hydrocarbon group, saturated or unsaturated, optionally branched", is taken to mean any non-aromatic hydrocarbon group comprising at least one ring, said ring comprising 3 to 8 carbon atoms, said ring being able to be saturated or, on the contrary, to comprise one or more unsaturations, this or these rings moreover being able to be branched, the branched chain(s) then comprising from 1 to 6 carbon atoms. Thus, this group may notably be a cycloalkyl group (cyclopropane, cyclopentane, cyclohexane, etc.), a cycloalkenyl group (cyclopropenyl, cyclopentenyl, cyclohexenyl, etc.) or instead a cycloalkynyl group;

"$C_3$ to $C_8$ cyclic hydrocarbon group, saturated or unsaturated, optionally branched" is taken to mean any non-aromatic hydrocarbon group comprising at least one ring as defined in the preceding paragraph as well as any aromatic hydrocarbon group comprising at least one ring, said ring comprising from 3 to 8 carbon atoms and satisfying the Mickel aromaticity rule with a number of delocalised π electrons equal to 4n+2. This or these rings may moreover be branched, the branched chain(s) then comprising from 1 to 6 carbon atoms. Thus, this group may notably be a cycloalkyl group, a cycloalkenyl group, a cycloalkynyl group or instead a cycloaromatic group such as a phenyl or benzyl group.

Moreover, the expression "from . . . to . . . " that has been used to define intervals, and which is used in the remainder of the present application, must be understood as defining not only the values of the interval, but also the values of the limits of said interval.

The Inventors have in fact observed that, in a surprising and unexpected manner, the use of compounds of the general formula (I) above make it possible to extract, in an efficient and selective manner, at least one rare earth present, and advantageously at least one lanthanide present, in an aqueous solution comprising, moreover, phosphoric acid.

Yet, although some of the compounds of the general formula (I) above have already been the subject of extraction tests, as reported in the publication, referenced [3], of M. Iqbal et al. ("*Synthesis and evaluation of ligands with mixed amide and phosphonate, phosphinoxide, and phosphonothioate sites for An(III)/Ln(III) extraction*", New J. Chem., 2012, 36, 2048-2059), these extractions were carried out in conditions similar to those described in the publications [1] and [2], namely from aqueous phases comprising nitric acid, and not phosphoric acid.

In an advantageous version, the compound of general formula (I), the use of which is the subject of the present invention, is the compound in which n=0 and of the following general formula (I'):

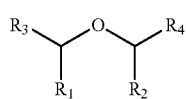

(I')

where $R_1$, $R_2$, $R_3$ and $R_4$ are as defined above.

In a first more specifically advantageous version, the present invention relates to the use of the compound of the following specific formula (I-a):

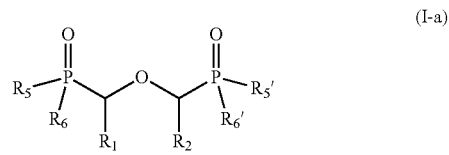

(I-a)

where $R_1$, $R_2$, $R_5$, $R_6$, $R_5'$ and $R_6'$ are as defined above, it being specified that $R_5$ and/or $R_6$ are a hydroxyl group —OH.

In a preferential manner, in the specific formula (I-a) above:

one of $R_5$ and $R_6$ is a hydroxyl group —OH and the other one of $R_5$ and $R_6$ is an alkoxyl group —OR, with R being a $C_2$ to $C_8$, advantageously $C_4$, alkyl group, linear or branched, and $R_5'$ and $R_6'$ are, independently of each other, a $C_4$ to $C_{10}$, advantageously $C_8$, alkyl group, linear or branched.

The compound of specific formula (I-a), in which $R_5$, $R_6$, $R_5'$ and $R_6'$ are as defined above, corresponds to a bifunctional compound comprising a phosphinate group —PO(OH)(OR) and a phosphine oxide group —POR$_5'$R$_6'$.

Also in a preferred manner, in the specific formula (I-a) above, and according to a first alternative embodiment, $R_1$ and $R_2$ are each a hydrogen atom.

As demonstrated in example 9 hereafter, the use of such a bifunctional compound comprising a phosphinate group and a phosphine oxide group and in which $R_1$=$R_2$=H makes it possible to extract heavy rare earths (such as ytterbium Yb) in an efficient and particularly selective manner, whether with respect to rare earths of lower atomic number (such as La, Nd, Gd and Dy) or impurities (represented in all the examples by Fe), and regardless of the concentration of phosphoric acid.

Also in a preferred manner, in the specific formula (I-a) above, and according to a second alternative embodiment, at least one of $R_1$ and $R_2$ is a $C_1$ to $C_{10}$, advantageously $C_1$ to $C_8$, alkyl group, linear or branched.

Thus, and according to a first aspect of this second alternative embodiment, in the specific formula (I-a) above, $R_1$ and $R_2$ are each a $C_1$ to $C_{10}$, advantageously $C_1$ to $C_8$, alkyl group, linear or branched.

According to a second aspect of this second alternative embodiment, in the specific formula (I-a) above, one of $R_1$ and $R_2$ is a hydrogen atom and the other one of $R_1$ and $R_2$ is a $C_1$ to $C_{10}$, advantageously $C_1$ to $C_8$, alkyl group, linear or branched.

In a second more particularly advantageous version, the present invention relates to the use of the compound of the following specific formula (I-b):

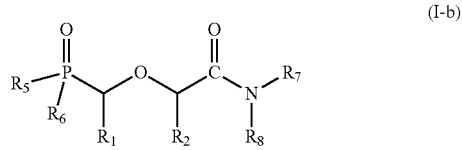

(I-b)

where $R_1$, $R_2$, $R_5$, $R_6$, $R_7$ and $R_8$ are as defined above, it being specified that $R_5$ and/or $R_6$ are a hydroxyl group —OH.

In a preferential manner, in the specific formula (I-b) above:
one of $R_5$ and $R_6$ is a hydroxyl group —OH and the other one of $R_5$ and $R_6$ is a $C_4$ to $C_{10}$, advantageously $C_8$, alkyl group, linear or branched, or an alkoxyl group —OR, with R being a $C_2$ to $C_8$, advantageously $C_4$, alkyl group, linear or branched, and $R_7$ and $R_8$ are preferentially, independently of each other, a $C_4$ to $C_{10}$, advantageously $C_8$, alkyl group, linear or branched.

Thus, in the case where one of $R_5$ and $R_6$ is —OH, the other one of $R_5$ and $R_6$ is an alkyl group, linear or branched, as specified above and $R_7$ and $R_8$ are as defined above, the compound of specific formula (I-b) corresponds to a bifunctional compound comprising a phosphinate group —PO(OH)$R_6$ or —PO(OH)$R_5$ and an amide group —$COR_7R_8$.

Thus, in the case where one of $R_5$ and $R_6$ is —OH, the other one of $R_5$ and $R_6$ is an alkoxyl group —OR as specified above and $R_7$ and $R_8$ are as defined above, the compound of specific formula (I-b) corresponds to a bifunctional compound comprising a phosphonate group —PO(OH)(OR) and an amide group —$COR_7R_8$.

Also in a preferred manner, in the specific formula (I-b) above, and according to a first alternative embodiment, $R_1$ and $R_2$ are each a hydrogen atom.

As demonstrated in examples 11 and 12 hereafter, the use of such a bifunctional compound comprising a phosphonate group and an amide group and in which $R_1=R_2=H$ makes it possible to extract, in a grouped manner, all of the heavy rare earths tested (Gd, Dy and Yb) as well as certain light rare earths (Nd, but not La), and regardless of the concentration of phosphoric acid of the aqueous phase, the extraction of Yb being moreover particularly selective with respect to impurities (Fe).

Also in a preferred manner, in the specific formula (I-b) above, and according to a second alternative embodiment, at least one of $R_1$ and $R_2$ is a $C_1$ to $C_{10}$, advantageously $C_1$ to $C_8$, alkyl group, linear or branched.

Thus, and according to a first aspect of this second alternative embodiment, in the specific formula (I-b) above, $R_1$ and $R_2$ are each a $C_1$ to $C_{10}$, advantageously $C_1$ to $C_8$, alkyl group, linear or branched.

According to a second aspect of this second alternative embodiment, in the specific formula (I-b) above, one of $R_1$ and $R_2$ is a hydrogen atom and the other one of $R_1$ and $R_2$ is a $C_1$ to $C_{10}$, advantageously $C_1$ to $C_8$, alkyl group, linear or branched.

According to the second aspect of this second alternative embodiment, the compound of specific formula (I-b), the use of which is the subject of the present invention, may comprise a branching in alpha position with respect to the ether, either on the side of the phosphonate group (in which case $R_2$=H), or on the side of the amide group (in which case $R_1$=H).

According to this second aspect, the compound of specific formula (I-b) is advantageously that in which $R_2$ is a hydrogen atom.

Typically, and with reference to what has been described, the compounds having the general formula (I) and, among them, the compounds having the specific formulas (I-a) and (I-b), are used, according to the present invention, as extraction agents for extracting at least one rare earth from an aqueous phase in which said at least one rare earth is present, said aqueous phase comprising, moreover, phosphoric acid.

According to an advantageous alternative embodiment of the invention, the aqueous phase is an acid digestion solution, typically by one or more inorganic acids, of a concentrate of a natural or urban ore comprising said at least one rare earth. The presence of phosphoric acid in this acid digestion solution results from the use of phosphoric acid as inorganic acid and/or from its formation in situ given the presence of precursors of such an acid, such as natural phosphates.

It will be recalled that urban ore may notably come from the recycling of industrial wastes such as electrical and electronic equipment waste (3EW).

According to another advantageous alternative embodiment of the invention, the aqueous phase comprises at least 0.1 mol/L, advantageously from 0.2 mol/L to 8 mol/L, and preferentially from 0.5 mol/L to 5 mol/L, of phosphoric acid.

According to another advantageous alternative embodiment of the invention, the extraction is carried out by the technique of liquid-liquid extraction, a technique which brings this aqueous phase comprising the rare earth(s), advantageously the lanthanide(s), and phosphoric acid into contact with an organic phase comprising one or more of the compounds mentioned above, preferentially a single of these compounds.

According to another advantageous alternative embodiment of the invention, this liquid-liquid extraction is carried out by means of an organic phase comprising at least $10^{-3}$ mol/L, advantageously from $5 \cdot 10^{-3}$ mol/L to 1 mol/L, and preferentially from $10^{-2}$ mol/L to $10^{-1}$ mol/L, of the compound in solution in an organic diluent.

Said organic diluent is advantageously of aliphatic type, and may notably be n-docedane, hydrogenated tetrapropylene (HTP), kerosene or an isoparaffin such as Isane® IP 185 sold by the Total company.

The present invention relates, secondly, to a method for recovering at least one rare earth present, and advantageously at least one lanthanide present, in an aqueous phase, said aqueous phase further comprising phosphoric acid.

According to the invention, this recovery method comprises the following steps:

a) extracting said at least one rare earth, advantageously said at least one lanthanide, from the aqueous phase by bringing the aqueous phase into contact with an organic phase comprising at least one compound as defined above, then separating the aqueous phase from the organic phase; and b) stripping said at least one rare earth present, advantageously said at least one lanthanide present, in the organic phase as obtained at the end of step a) by bringing said organic phase into contact with an aqueous phase, then separating the organic phase from the aqueous phase.

In step a) of this method according to the invention, the compound present in the organic phase is the compound as defined above, it being specified that the advantageous characteristics of this compound may be taken alone or in combination.

In the same way, the aqueous and organic phases used during step a) of the method according to the invention may be as defined above, in relation with the use of the compound, and may have the advantageous characteristics described above for these aqueous and organic phases, alone or in combination.

In an advantageous alternative embodiment of the method according to the invention, during step a), to the aqueous phase is added at least one salt, such as a nitrate or sulphate salt of an alkaline or alkaline-earth metal, which makes it possible to increase the ionic force of said aqueous solution.

The introduction of such a salt has the effect of increasing the extraction performance for all of the rare earths (see examples 11 and 12 hereafter).

Such a salt may notably be selected from sodium, lithium or potassium nitrate. Said salt is advantageously sodium nitrate.

The molar concentration of salt(s), in the aqueous phase, is from 0.01 mol/L to 4 mol/L, advantageously from 0.05 mol/L to 3 mol/L and, preferentially, from 0.1 mol/L to 2 mol/L.

In an alternative advantageous embodiment of the method according to the invention, the aqueous phase used during step a) is an acid digestion solution, by phosphoric acid, of a concentrate of a natural or urban ore comprising said at least one rare earth.

The present invention relates, thirdly, to specific compounds which, to the knowledge of the Inventors, have not been described to date.

In a first version, the compound according to the invention has the following specific formula (I-a):

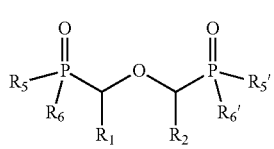

(I-a)

where
  $R_1$ and $R_2$ are, independently of each other, a hydrogen atom, a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched,
  one of $R_5$ and $R_6$ is a hydroxyl group —OH and the other one of $R_5$ and $R_6$ is a $C_1$ to $C_{12}$ aliphatic hydrocarbon group, saturated or unsaturated, linear or branched, a $C_3$ to $C_8$ cyclic hydrocarbon group, saturated or unsaturated, optionally branched, a hydroxyl group —OH or an alkoxyl group —OR, with R being a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched, and
  $R_5'$ and $R_6'$ are, independently of each other, a $C_1$ to $C_{12}$ aliphatic hydrocarbon group, saturated or unsaturated, linear or branched, a $C_3$ to $C_8$ cyclic hydrocarbon group, saturated or unsaturated, optionally branched, a hydroxyl group —OH or an alkoxyl group —OR', with R' being a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched.

In a preferential manner, in the specific formula (I-a) above:
  one of $R_5$ and $R_6$ is a hydroxyl group —OH and the other one of $R_5$ and $R_6$ is an alkoxyl group —OR, with R being a $C_2$ to $C_8$, advantageously $C_4$, alkyl group, linear or branched, and
  $R_5'$ and $R_6'$ are, independently of each other, a $C_4$ to $C_{10}$, advantageously $C_8$, alkyl group, linear or branched.

As already indicated previously, the compound of specific formula (I-a) in which $R_5$, $R_6$, $R_5'$ and $R_6'$ are as they have been defined above, corresponds to a bifunctional compound comprising a phosphonate group —PO(OH)(OR) and a phosphine oxide group —POR$_5$'R$_6$'.

Also in a preferred manner, in the specific formula (I-a) above, and according to a first alternative embodiment, $R_1$ and $R_2$ are each a hydrogen atom.

Also in a preferred manner, in the specific formula (I-a) above, and according to a second alternative embodiment, at least one of $R_1$ and $R_2$ is a $C_1$ to $C_{10}$, advantageously $C_1$ to $C_8$, alkyl group, linear or branched.

Thus, and according to a first aspect of this second alternative embodiment, in the specific formula (I-a) above, $R_1$ and $R_2$ are each a $C_1$ to $C_{10}$, advantageously $C_1$ to $C_8$, alkyl group, linear or branched.

According to a second aspect of this second alternative embodiment, in the specific formula (I-a) above, one of $R_1$ and $R_2$ is a hydrogen atom and the other one of $R_1$ and $R_2$ is a $C_1$ to $C_{10}$, advantageously $C_1$ to $C_8$, alkyl group, linear or branched.

In a second version, the compound according to the invention has the following specific formula (I-b):

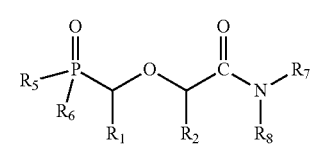

(I-b)

where
  $R_1$ and $R_2$ are, independently of each other, a hydrogen atom, a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched,
  one of $R_5$ and $R_6$ is a hydroxyl group —OH and the other one of $R_5$ and $R_6$ is a $C_1$ to $C_{12}$ aliphatic hydrocarbon group, saturated or unsaturated, linear or branched, a $C_3$ to $C_8$ cyclic hydrocarbon group, saturated or unsaturated, optionally branched, a hydroxyl group —OH or an alkoxyl group —OR, with R being a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched, and
  $R_7$ and $R_8$ are, independently of each other, a hydrogen atom, a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched.

In a preferential manner, in the specific formula (I-b) above, $R_5$ and $R_6$ are such that:
  one of $R_5$ and $R_6$ is a hydroxyl group —OH and the other one of $R_5$ and $R_6$ is a $C_4$ to $C_{10}$, advantageously $C_8$, alkyl group, linear or branched, or an alkoxyl group —OR, with R being a $C_2$ to $C_8$, advantageously $C_4$, alkyl group, linear or branched, and
  $R_7$ and $R_8$ are, independently of each other, a $C_4$ to $C_{10}$, advantageously $C_8$, alkyl group, linear or branched.

Thus, and as already indicated previously, the compound of specific formula (I-b) may correspond to a bifunctional compound which comprises:
  either a phosphinate group —PO(OH)R$_6$ or —PO(OH)R$_5$ and an amide group —COR$_7$R$_8$, in the case where one of $R_5$ and $R_6$ is —OH and the other one of $R_5$ and $R_6$ is an alkyl group as specified above, or a phosphonate group —PO(OH)(OR) and an amide group —COR$_7$R$_8$, in the case where one of R$_5$ and R$_6$ is —OH and the other one of R$_5$ and R$_6$ is an alkoxyl group —OR as specified above.

Also in a preferred manner, in the specific formula (I-b) above, and according to a first alternative embodiment, R$_1$ and R$_2$ are each a hydrogen atom.

Also in a preferred manner, in the specific formula (I-b) above, and according to a second alternative embodiment, at least one of R$_1$ and R$_2$ is a C$_1$ to C$_{10}$, advantageously C$_1$ to C$_8$, alkyl group, linear or branched.

Thus, and according to a first aspect of this second alternative embodiment, in the specific formula (I-b) above, R$_1$ and R$_2$ are each a C$_1$ to C$_{10}$, advantageously C$_1$ to C$_8$, alkyl group, linear or branched.

According to a second aspect of this second alternative embodiment, in the specific formula (I-b) above, one of R$_1$ and R$_2$ is a hydrogen atom and the other one of R$_1$ and R$_2$ is a C$_1$ to C$_{10}$, advantageously C$_1$ to C$_8$, alkyl group, linear or branched.

According to the second aspect of this second alternative embodiment, the compound of specific formula (I-b), the use of which is the subject of the present invention, may comprise a branching in alpha position with respect to the ether, either on the side of the phosphonate group (in which case R$_2$=H), or on the side of the amide group (in which case R$_1$=H).

According to this second aspect, the compound of specific formula (I-b) is advantageously that in which R$_2$ is a hydrogen atom.

Other characteristics and advantages of the invention will become clearer on reading the examples that follow and which relate to the synthesis of compounds according to the invention as well as to tests which demonstrate the aptitude of these compounds to extract all or part of rare earths from aqueous solutions comprising phosphoric acid and in which said rare earths are present.

It is specified that these examples are only given for the purposes of illustrating the objects of the invention and do not constitute in any case a limitation of said objects.

EXAMPLES

Synthesis of Compounds According to the Invention

Example 1: Synthesis of a Bis-Phosphine Oxide

The synthesis implements an alcohol-phosphine oxide with a chloride-phosphine oxide, according to the Williamson reaction, in the presence of sodium hydride (NaH) in tetrahydrofuran (THF).

The corresponding reaction, noted (1), is the following:

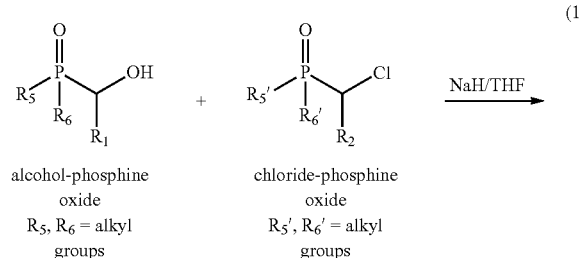

(1)

alcohol-phosphine oxide
R$_5$, R$_6$ = alkyl groups chloride-phosphine oxide
R$_5'$, R$_6'$ = alkyl groups

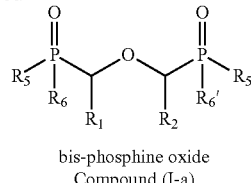

bis-phosphine oxide
Compound (I-a)

More particularly, the synthesis targeted here is that of bis-di-octyl phosphine oxide, which corresponds to the compound of formula (I-a) in which R$_1$=R$_2$=H and R$_5$=R$_6$=R$_5'$=R$_6'$=n-C$_8$H$_{17}$=n-octyl (hereafter abbreviated to "Oct").

Bis-di-octyl phosphine oxide is obtained by the implementation of the following reaction (2):

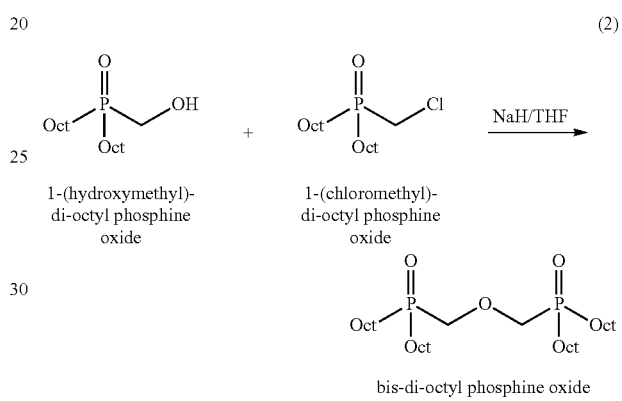

(2)

1-(hydroxymethyl)-di-octyl phosphine oxide 1-(chloromethyl)-di-octyl phosphine oxide bis-di-octyl phosphine oxide 1.1 Synthesis of 1-(hydroxymethyl)-di-octyl phosphine oxide The synthesis of 1-(hydroxymethyl)-di-octyl phosphine oxide is carried out from di-octyl phosphine oxide, this di-octyl phosphine oxide being itself synthesised from a phosphite.

1.1.1 Synthesis of di-octyl phosphine oxide

Di-octyl phosphine oxide is synthesised from diethyl phosphite, according to the following reaction (3):

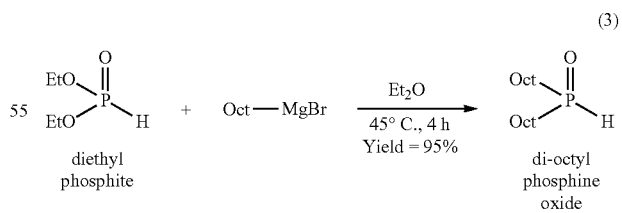

(3)

diethyl phosphite di-octyl phosphine oxide

The operating protocol followed for the implementation of the reaction (3) is the following: to a 2 mol/L suspension of n-octyl magnesium bromide (noted Oct-MgBr) in ether (100 mL, i.e. around 3 eq) is added drop by drop, at 0° C. and under stirring, diethyl phosphite (1 eq, i.e. 13.5 g or 70 mmol). After total addition, the mixture is slowly taken to room temperature then to 45° C. for 4 h. The mixture is next acidified using a 25% aqueous solution of sulphuric acid H₂SO₄ added drop by drop at 0° C. Once the effervescence has stopped, a same quantity of water and of ether is added to the mixture. The organic phase is next separated and washed successively with a 10% solution of potassium carbonate K₂CO₃ (2 times), with water (2 times) then with brine (2 times). The organic phase is next dried over sodium sulphate Na₂SO₄, filtered then concentrated to obtain di-octyl phosphine oxide (95% yield) which is in the form of a white powder.

The characterisation data of this di-octyl phosphine oxide are the following:

$^1$H NMR (400 MHz, CDCl₃) δ (ppm): 7.38 (d, 1H, P—H); 1.82-1.53 (m, 8H, CH₂—CH₂—P); 1.41-1.22 (m, 20H, CH₂); 0.85 (m, 6H, CH₃)

$^{31}$P NMR (160 MHz, CDCl₃) δ (ppm): 35.3

1.1.2 Synthesis of 1-(hydroxymethyp-di-octyl phosphine oxide 1-(hydroxymethyl)-di-octyl phosphine oxide is synthesised from the di-octyl phosphine oxide as previously obtained (see paragraph 1.1.1), according to the following reaction (4):

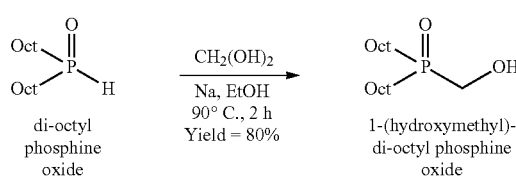

The operating protocol followed for the implementation of the reaction (4) is the following: to a solution of di-octyl phosphine oxide (1 eq) in ethanol (0.5 mol/L), are added, under stirring, sodium Na (activated beforehand in methanol) then paraformaldehyde (1.2 eq). The mixture is next taken to reflux (80° C.) for 2 h. The solvent is next evaporated. The mixture is then taken up in dichloromethane (DCM), then washed with water (2 times) and with brine (2 times). The organic phase is dried over Na₂SO₄, filtered and concentrated to obtain 1-(hydroxymethyl)-di-octyl phosphine oxide (80% yield) which is in the form of a very viscous oil.

The characterisation data of this 1-(hydroxymethyl)-di-octyl phosphine oxide are the following:

$^1$H NMR (400 MHz, CDCl₃) δ (ppm): 3.89 (s, 2H, CH₂—OH); 1.80-1.72 (m, 4H, CH₂—P); 1.64-1.55 (m, 4H, CH₂—CH₂—P); 1.42-1.27 (m, 20H, CH₂); 0.90 (m, 6H, CH₃)

$^{31}$P NMR (160 MHz, CDCl₃) δ (ppm): 49.1

1.2 Synthesis of 1-(chloromethyl)-di-octyl phosphine oxide

The synthesis of 1-(chloromethyl)-di-octyl phosphine oxide is carried out from 1-(hydroxymethyl)-di-octyl phosphine oxide as previously obtained (see paragraph 1.1.2), according to the following reaction (5):

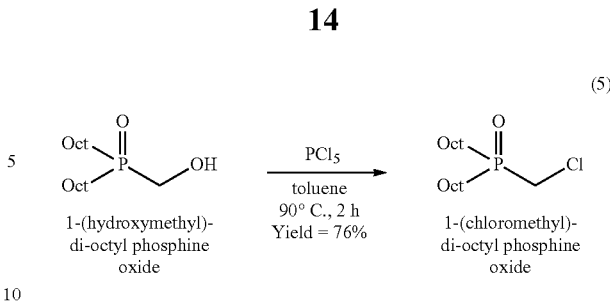

The operating protocol followed for the implementation of the reaction (5) is the following: to a solution formed of 1-(hydroxymethyl)-di-octyl phosphine oxide (1 eq) in anhydrous toluene (0.5 mol/L) is added, at 0° C. and under stirring, phosphorous pentachloride PCl₅ (2 eq) in small portions. After total addition, the mixture is slowly taken to room temperature then to reflux (110° C.) for 2 h. The excess of PCl₅ is next neutralised by adding, drop by drop, water at 0° C. Once the effervescence has stopped, a quantity of water equal to half of the volume of toluene is added and the mixture is stirred for 10 min. The organic phase is next separated and washed with a solution of sodium hydroxide NaOH (0.5M) and brine. It is next dried over Na₂SO₄, filtered and concentrated to obtain 1-(chloromethyl)-di-octyl phosphine oxide (76% yield) which is in the form of a viscous oil.

The characterisation data of this 1-(chloromethyl)-di-octyl phosphine oxide are the following:

$^1$H NMR (400 MHz, CDCl₃) δ (ppm): 3.58 (d, 2H, J=8 Hz, CH₂—Cl); 1.91-1.82 (m, 4H, CH₂—P); 1.74-1.56 (m, 4H, CH₂—CH₂—P); 1.48-1.26 (m, 20H, CH₂); 0.90 (m, 6H, CH₃)

$^{31}$P NMR (160 MHz, CDCl₃) δ (ppm): 49.3

1.3 Synthesis of bis-di-octyl phosphine oxide

The synthesis of bis-di-octyl phosphine oxide is obtained by the reaction of 1-(hydroxymethyl)-di-octyl phosphine oxide and 1-(chloromethyl)-di-octyl phosphine oxide previously synthesised (see respectively paragraphs 1.1 and 1.2 above), according to the following reaction (2'):

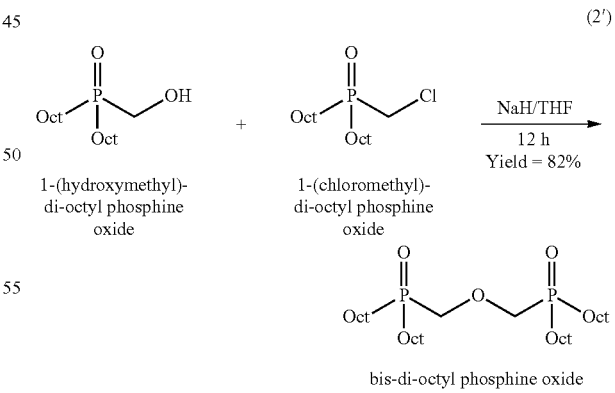

The operating protocol followed for the implementation of this reaction (2') is the following: to a suspension of sodium hydride NaH (4 eq, washed beforehand 2 times with pentane) in anhydrous THF (1 mol/L), is added drop by drop a solution formed by 1-(hydroxymethyl)-di-octyl phosphine oxide in THF (1 eq at 0.5 mol/L). After total addition, the mixture is stirred for 1 h then a solution formed by 1-(chloromethyl)-di-octyl phosphine oxide (1.2 eq) in THF is added drop by drop. The mixture is next stirred for 12 h. The crude is next acidified using a solution of hydrochloric aciid HCl (3M), added drop by drop at 0° C. The solvent is next evaporated. The crude is taken up in ethyl acetate then washed with HCl (3M) (2 times) and water (2 times). The organic phase is dried over $Na_2SO_4$, filtered then concentrated in a rotary evaporator. The resulting crude is next purified by recrystallisation in ethyl acetate to obtain bis-di-octyl phosphine oxide (with a 82% yield) which is in the form of a white powder.

The characterisation data of this bis-di-octyl phosphine oxide are the following:

$^1$H NMR (400 MHz, $CDCl_3$) δ (ppm): 3.90 (d, 4H, J=6.4 Hz, $CH_2$—O); 1.78-1.57 (m, 16H, $CH_2$—$CH_2$—P); 1.42-1.27 (m, 40H, $CH_2$); 0.90 (m, 12H, $CH_3$)

$^{31}$P NMR (160 MHz, $CDCl_3$) S (ppm): 46.1

Example 2: Synthesis of a Phosphonate-Phosphine Oxide

The synthesis implements an alcohol-phosphonate with a chloride-phosphine oxide, according to the Williamson reaction, in the presence of sodium hydride (NaH) and potassium iodide (KI) in tetrahydrofuran (THF).

The corresponding reaction, noted (ibis), is the following, it being specified that one of the alkoxyl groups among $R_5$ and $R_6$ hydrolyses during this reaction:

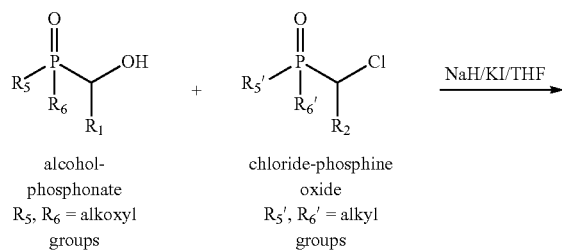

More particularly, the synthesis targeted here is that of butyl ((((dioctanoylphosphoryl)-2-oxoethoxy)methyl)-phosphonate, which corresponds to the compound of formula (I-a) in which $R_1$=$R_2$=H, one of $R_5$ and $R_6$ is a —OH and the other one of $R_5$ and $R_6$ is n-$C_4H_9O$ (hereafter abbreviated to "BuO") and $R_5'$=$R_6'$=n-octyl (hereafter abbreviated to "Oct").

Butyl (((dioctanoylphosphoryl)-2-oxoethoxy)methyl)-phosphonate is obtained by the implementation of the following reaction (6):

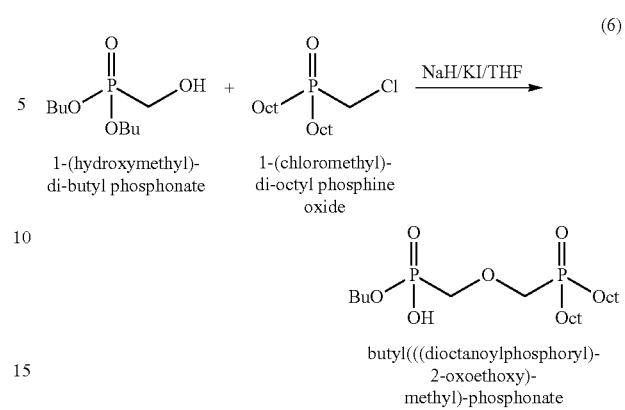

2.1 Synthesis of 1-(hydroxymethyp-di-butyl-phosphonate

The synthesis of 1-(hydroxymethyl)-di-butyl-phosphonate is carried out from a phosphite, in this case dibutyl phosphite, according to the following reaction (7):

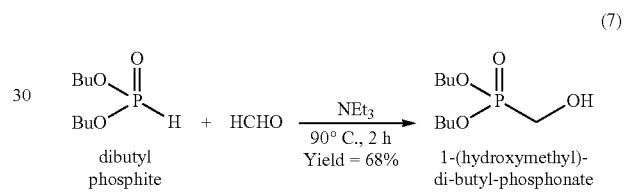

The operating protocol followed for the implementation of the reaction (7) is the following: a mixture of dibutyl phosphite (1 eq) and formaldehyde (1.2 eq) in triethylamine $NEt_3$ is taken to reflux (90° C.) under stirring for 2 h. The triethylamine is next evaporated. The crude is taken up in DCM then washed with a saturated solution of $NaHCO_3$ (2 times) and with brine (2 times). The organic phase is dried over $Na_2SO_4$ then concentrated in a rotary evaporator. The excess of formaldehyde is distilled in an oven at reduced pressure. The resulting crude is next purified by flash chromatography on silica gel column (eluant: cyclohexane/ethyl acetate from 100/50 to 50/100, v/v) to obtain 1-(hydroxymethyl)-di-butyl-phosphonate (68% yield) which is in the form of a viscous oil.

The characterisation data of this 1-(hydroxymethyl)-di-butyl-phosphonate are the following:

$^1$H NMR (400 MHz, $CDCl_3$) δ (ppm): 4.84 (s, 1H, OH); 4.14-4.08 (m, 2H, O—$CH_2$); 3.92 (d, 4H, J=6 Hz, $CH_2$—OH); 1.71-1.64 (m, 4H, O—$CH_2$—$CH_2$); 1.47-1.37 (m, 4H, O—$CH_2$—$CH_2$—$CH_2$); 0.95 (t, 6H, J=7.4 Hz, $CH_3$)

$^{31}$P NMR (160 MHz, $CDCl_3$) δ (ppm): 24.5

2.2 Synthesis of 1-(chloromethyl)-di-octyl phosphine oxide

The synthesis of 1-(chloromethyl)-di-octyl phosphine oxide is carried out according to reaction (5) and to the operating protocol described in paragraph 1.2 above.

2.3 Synthesis of butyl (((dioctanoylphosphoryl)-2-oxoethoxy)methyl)-phosphonate

The synthesis of butyl (((dioctanoylphosphoryl)-2-oxoethoxy)methyl)-phosphonate is obtained by the reaction of 1-(hydroxymethyl)-di-butyl phosphonate and 1-(chloromethyl)-di-octyl phosphine oxide previously synthesised (see respectively paragraphs 2.1 and 1.2 above), according to the following reaction (6'):

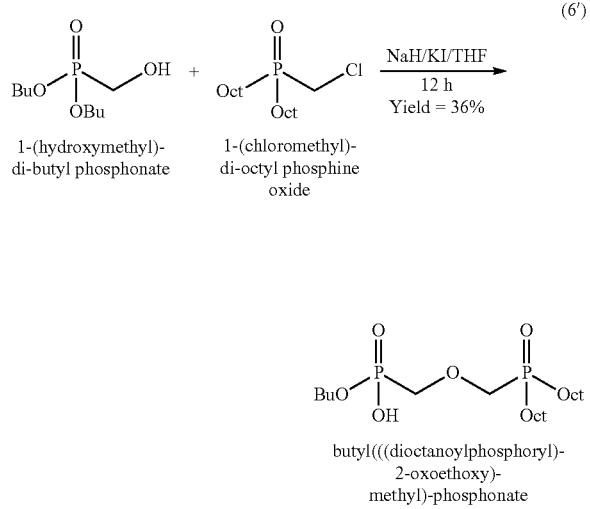

(6')

The operating protocol followed for the implementation of this reaction (6') is the following: to a suspension of sodium hydride NaH (4 eq, washed beforehand 2 times with pentane) in anhydrous THF (1 mol/L), and in the presence of potassium iodide KI (1 eq), is added drop by drop a solution formed by 1-(hydroxymethyl)-di-butyl phosphonate in THF (1 eq at 0.5 mol/L). After total addition, the mixture is stirred for 1 h, then is added drop by drop a solution formed by 1-(chloromethyl)-di-octyl phosphine oxide (1.2 eq) in THF. The mixture is next stirred for 12 h. The crude is next acidified using a solution of hydrochloric acid HCl (3M), added drop by drop at 0° C. The solvent is next evaporated. The crude is taken up in ethyl acetate then washed with HCl (3M) (2 times) and with water (2 times). The organic phase is dried over $Na_2SO_4$, filtered then concentrated in a rotary evaporator. The resulting crude is next purified by recrystallisation in ethyl acetate to obtain butyl ((dioctanoylphosphoryl)-2-oxoethoxy)methyl)-phosphonate (with a 36% yield) which is in the form of a white powder.

The characterisation data of this butyl ((dioctanoylphosphoryl)-2-oxoethoxy)methyl)-phosphonate are the following:

$^1$H NMR (400 MHz, $CDCl_3$) δ (ppm): 9.68 (s, 1H, OH); 4.17-4.05 (m, 4H, $CH_2$—O and O—$CH_2$—P—O); 3.95 (d, 2H, J=7.6 Hz, P—$CH_2$—O); 1.86-1.78 (m, 4H, $CH_2$—P); 1.71-1.55 (m, 6H, $CH_2$—$CH_2$—P and O—$CH_2$—$CH_2$); 1.47-1.25 (m, 22H, $CH_2$); 0.97-0.87 (m, 9H, $CH_3$)

$^{31}$P NMR (160 MHz, $CDCl_3$) δ (ppm): 51.9; 19.8

HRMS (EI+): calculated for $C_{22}H_{48}O_5P_2$: 454.3055; found: 454.3055

Example 3: Synthesis of a Phosphinate

Ethyl octanoyl-phosphinate, or octyl ethoxyphosphinate, is synthesised from triethyl phosphite, according to the following reaction (8):

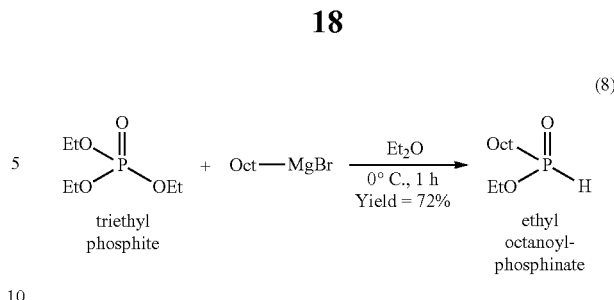

The operating protocol followed for the implementation of the reaction (8) is the following: to a 2 mol/L suspension of n-octyl magnesium bromide (noted Oct-MgBr) in ether (20 mL, i.e. around 1.5 eq) is added drop by drop, over a period of 1 h, at 0° C. and under argon atmosphere, triethyl phosphite (10 mL or 57.5 mmol). After total addition, the mixture is vigorously stirred, then a solution of 1M HCl (50 mL) is added up to complete dissolution of the salts (the addition of ether may optionally be necessary). The mixture is slowly taken to room temperature then to 45° C. for 4 h. The mixture is next extracted with 100 mL of ether (2 times). The organic phase is next separated and washed successively with 100 mL of 1M HCl, with 100 mL of water then with 100 mL of brine. The organic phase is next dried over $MgSO_4$, and the solvent is evaporated. After purification by flash chromatography on silica gel column (eluant: cyclohexane/ethyl acetate), ethyl octanoyl-phosphinate (72% yield), which is in the form of a colourless oil, is isolated.

The characterisation data of this ethyl octanoyl-phosphinate are the following:

$^1$H NMR (400 MHz, $CDCl_3$) δ (ppm): 7.04 (d, 1H, P—H); 4.22-4.05 (m, 2H, O—$CH_2$); 1.81-1.73 (m, 2H, P—$CH_2$); 1.65-1.54 (m, 2H, P—$CH_2$—$CH_2$); 1.42-1.24 (m, 13H, $CH_2$ and O—$CH_2$—$CH_3$); 0.89 (t, 3H, J=7 Hz, $CH_3$)

$^{31}$P NMR (160 MHz, $CDCl_3$) δ (ppm): 39.0

Example 4: Synthesis of Alcohol-Phosphonates

An alcohol-phosphonate may be obtained by the reaction of a phosphite with an aldehyde according to the following reaction (9):

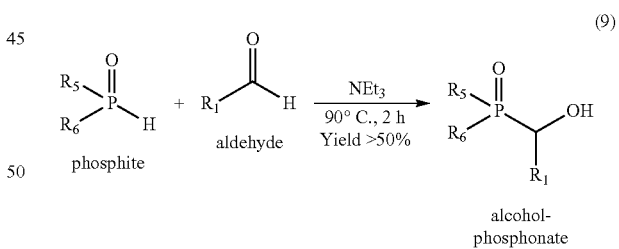

Thus, as has been seen already in paragraph 2.1 above, 1-(hydroxymethyl)-di-butyl phosphonate was synthesised by the reaction of dibutyl phosphite ($R_5$=$R_6$=$C_4H_9O$) with formaldehyde ($R_1$=H).

Other alcohol-phosphonates have been synthesised according to the following operating protocol: a mixture of phosphite (1 eq) and aldehyde (1.2 eq) in triethylamine is taken to reflux (90° C.) under stirring for 2 h. The triethylamine is next evaporated. The crude is taken up in DCM then washed with a saturated solution of $NaHCO_3$ (2 times) and with brine (2 times). The organic phase is dried over $Na_2SO_4$ then concentrated in a rotary evaporator. The excess of formaldehyde is distilled in an oven under reduced pressure. The resulting crude is next purified by flash chromatography on silica gel column (eluant: cyclohexane/ethyl acetate from 100/50 to 50/100, v/v) to obtain the corresponding alcohol-phosphonate (with a yield greater than 50%) which is in the form of a viscous oil or a white powder, depending on the case.

4.1 Synthesis of 1-(hydroxynonyl)-di-butyl-phosphonate 1-(hydroxynonyl)-di-butyl-phosphonate is the alcohol-phosphonate in which $R_5=R_6=$n-$C_4H_9O$ (BuO) and $R_1=$n-$C_8H_{17}$ (Oct). It thus corresponds to the following formula:

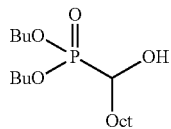

The characterisation data of this compound, synthesised with a 58% yield, are the following:

$^1$H NMR (400 MHz, CDCl$_3$) δ (ppm): 4.13-4.04 (m, 4H, O—CH$_2$); 3.85-3.80 (m, 1H, CH); 1.82-1.59 (m, 6H, CH$_2$); 1.42-1.24 (m, 16H, CH$_2$); 0.93-0.84 (m, 9H, CH$_3$)

$^{31}$P NMR (160 MHz, CDCl$_3$) δ (ppm): 25.4

4.2 Synthesis of 1-(hydroxyethyl)-di-butyl-phosphonate 1-(hydroxyethyl)-di-butyl-phosphonate is the alcohol-phosphonate in which $R_5=R_6=$n-$C_4H_9O$ (BuO) and $R_1=$CH$_3$. It thus corresponds to the following formula:

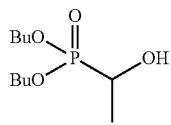

The characterisation data of this compound, synthesised with a 54% yield, are the following:

$^1$H NMR (400 MHz, CDCl$_3$) δ (ppm): 4.87 (s, 1H, OH); 4.07-3.95 (m, 5H, CH and O—CH$_2$); 1.62-1.54 (m, 4H, O—CH$_2$—CH$_2$); 1.38-1.28 (m, 7H, O—CH$_2$—CH$_2$—CH$_2$ and CH$_3$); 0.86 (t, 6H, J=7.4 Hz, CH$_3$)

$^{31}$P NMR (160 MHz, CDCl$_3$) δ (ppm): 25.8

4.3 Synthesis of 1-(hydroxymethyp-di-ethylhexyl-phosphonate 1-(hydroxymethyl)-di-ethylhexyl-phosphonate is the alcohol-phosphonate in which $R_5=R_6=$2-ethylhexyl (noted EtHex) and $R_1=$H. It thus corresponds to the following formula:

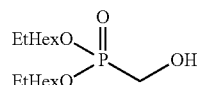

The characterisation data of this compound, synthesised with a 78% yield, are the following:

$^1$H NMR (400 MHz, CDCl$_3$) δ (ppm): 4.04-3.98 (m, 4H, O—CH$_2$); 3.92 (d, 2H, J=6 Hz, CH$_2$—OH); 1.60-1.54 (m, 2H, CH); 1.44-1.28 (m, 16H, CH$_2$); 0.91 (t, 6H, J=7.2 Hz, CH$_3$)

$^{31}$P NMR (160 MHz, CDCl$_3$) δ (ppm): 24.2

Example 5: Synthesis of an Alcohol-Phosphinate

An alcohol-phosphinate may be obtained by the reaction of a phosphinate with an aldehyde according to the following reaction (9'):

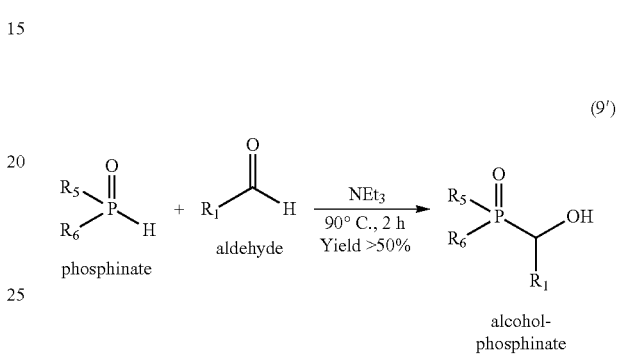

Thus, the synthesis of 1-(hydromethyl)-ethyl octanoyl-phosphinate is obtained by the reaction of ethyl octanoyl-phosphinate synthesised according to example 3 with formaldehyde.

1-(hydroxymethyl)-ethyl octanoyl-phosphinate is the alcohol-phosphinate in which $R_5=$n-$C_8H_{17}$ (Oct), $R_6=C_2H_5O$ (EtO) and $R_1=$H. It thus corresponds to the following formula:

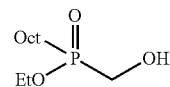

The characterisation data of this compound, synthesised with a 38% yield, are the following:

$^1$H NMR (400 MHz, CDCl$_3$) δ (ppm): 4.98 (s, 1H, OH); 4.14-4.08 (m, 2H, O—CH$_2$); 3.88-3.84 (m, 2H, CH$_2$—OH); 1.84-1.77 (m, 2H, P—CH$_2$); 1.64-1.56 (m, 2H, P—CH$_2$—CH$_2$); 1.40-1.27 (m, 13H, CH$_2$ and O—CH$_2$—CH$_3$); 0.88 (t, 3H, J=7.2 Hz, CH$_3$)

$^{31}$P NMR (160 MHz, CDCl$_3$) δ (ppm): 25.8

Example 6: Synthesis of Amido-Phosphonates

The synthesis of an amido-phosphonate implements an alcohol-phosphonate with a halide-amide, according to the Williamson reaction, in the presence of sodium hydride (NaH) and potassium iodide (KI) in tetrahydrofuran (THF).

The corresponding reaction, noted (10), is the following, it being specified that one of the alkoxyl groups of $R_5$ and $R_6$ hydrolyses during this reaction:

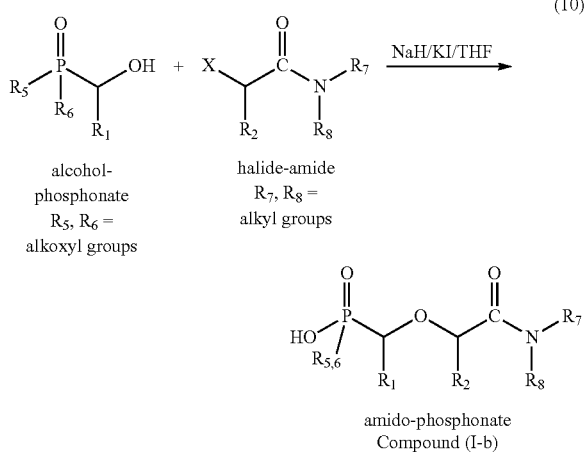

Several amido-phosphonate syntheses will now be described. These syntheses were all implemented according to the following operating protocol: to a suspension of NaH (4 eq, washed beforehand 2 times with pentane) in anhydrous THF (1 mol/L) is added, under stirring, KI (1 eq). The suspension is cooled to 0° C. and a solution of alcohol-phosphonate in THF (1 eq at 0.5 mol/L) is added drop by drop. After total addition, the mixture is stirred for 1 h at 0° C. then a solution of halide-amide (1.2 eq) in THF is added drop by drop. The mixture is next stirred for 6 h. The crude is next acidified using a saturated solution of ammonium chloride ($NH_4Cl$), added drop by drop at 0° C. Once the effervescence has stopped, a quantity of this solution equal to half of the volume in THF is added and the mixture is stirred for 15 min. The solvent is next evaporated. The crude is taken up in ethyl acetate then washed with saturated $NH_4Cl$ (2 times) and water (2 times). The organic phase is dried over $Na_2SO_4$ then concentrated in a rotary evaporator. The resulting crude is next purified by flash chromatography on silica gel column (eluant: ethyl acetate/methanol from 100/0 to 80/20, v/v) to obtain the corresponding amido-phosphonate which is in the form of a viscous oil.

6.1 Synthesis of butyl (((N,N-dioctylcarbamoyl)-2-oxoethoxy)methyl)-phosphonate The synthesis of butyl (((N,N-dioctylcarbamoyl)-2-oxoethoxy)methyl)-phosphonate is obtained by the reaction of the alcohol-phosphonate in which $R_5=R_6=n-C_4H_9O$ (BuO) and $R_1=H$ (see paragraph 2.1 above), with the halide-amide in which X=Cl, $R_7=R_8=n-C_8H_{17}$ (Oct) and $R_2=H$.

The corresponding reaction, noted (11), is the following:

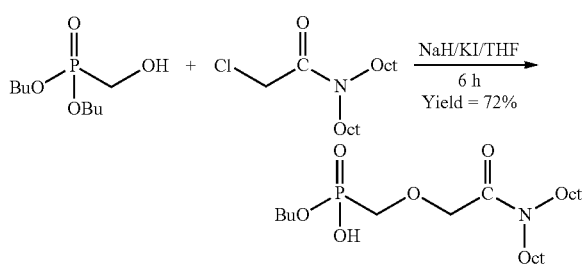

The characterisation data of this amido-phosphonate, synthesised with a 72% yield, are the following:
$^1$H NMR (400 MHz, $CDCl_3$) δ (ppm): 10.9 (s, 1H, OH); 4.34 (s, 2H, CO—$CH_2$—O); 4.14-4.08 (m, 2H, O—$CH_2$); 3.95 (d, 2H, J=8 Hz, P—$CH_2$—O); 3.30 (t, 2H, J=7.8 Hz, $CH_2$—N); 3.13 (t, 2H, J=7.8 Hz, $CH_2$—N); 1.70-1.63 (m, 2H, O—$CH_2$—$CH_2$); 1.58-1.50 (m, 4H, $CH_2$—$CH_2$—N); 1.44-1.37 (m, 2H, O—$CH_2$—$CH_2$—$CH_2$); 1.32-1.22 (m, 20H, $CH_2$); 0.94-0.86 (m, 9H, $CH_3$)
$^{31}$P NMR (160 MHz, $CDCl_3$) δ (ppm): 21.5
HRMS (EI+): calculated for $C_{23}H_{48}NO_5P$: 449.3348; found: 449.3348

6.2 Synthesis of butyl (((N,N-diethylhexylcarbamoyl)-2-oxoethoxy)methyl)-phosphonate The synthesis of butyl (((N,N-diethyllhexylcarbamoyl)-2-oxoethoxy)methyl)-phosphonate is obtained by the reaction of the alcohol-phosphonate in which $R_5=R_6=n-C_4H_9O$ (BuO) and $R_1=H$ (see paragraph 2.1 above), with the halide-amide in which X=Cl, $R_7=R_8$=2-ethyl hexyl (noted EtHex or HexEt) and $R_2=H$.

The corresponding reaction, noted (12), is the following:

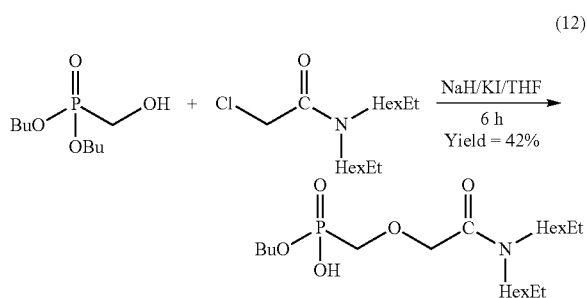

The characterisation data of this amido-phosphonate, synthesised with a 42% yield, are the following:
$^1$H NMR (400 MHz, $CDCl_3$) δ (ppm): 7.96 (s, 1H, OH); 4.37 (s, 2H, CO—$CH_2$—O); 4.17-4.07 (m, 2H, O—$CH_2$); 3.92 (d, 2H, J=8 Hz, P—$CH_2$—O); 3.40-3.20 (m, 2H, $CH_2$—N); 3.06-3.0 (m, 2H, $CH_2$—N); 1.72-1.56 (m, 4H, O—$CH_2$—$CH_2$ and CH); 1.47-1.37 (m, 2H, O—$CH_2$—$CH_2$—$CH_2$); 1.36-1.18 (m, 16H, $CH_2$); 0.96-0.86 (m, 15H, $CH_3$)
$^{31}$P NMR (160 MHz, $CDCl_3$) δ (ppm): 20.6
HRMS (EI+): calculated for $C_{23}H_{48}NO_5P$: 449.3348; found: 449.3348

6.3 Synthesis of butyl (((N,N-diethylhexylcarbamoyl)-2-oxoethoxy)nonyl)-phosphonate The synthesis of butyl (((N,N-diethylhexylcarbamoyl)-2-oxoethoxy)nonyl)-phosphonate is obtained by the reaction of the alcohol-phosphonate in which $R_5=R_6=n-C_4H_9O$ (BuO) and $R_1=n-C_8H_{17}$ (Oct) (see paragraph 4.1 above), with the halide-amide in which X=Cl, $R_7=R_8=n-C_8H_{17}$ (Oct) and $R_2=H$.

The corresponding reaction, noted (13), is the following:

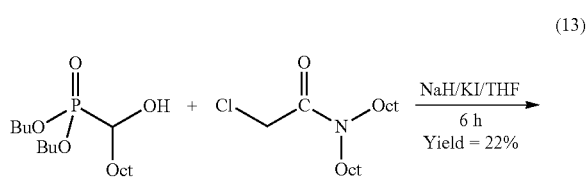

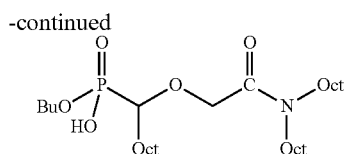

The characterisation data of this amido-phosphonate, synthesised with a 22% yield, are the following:

$^1$H NMR (400 MHz, CDCl$_3$) δ (ppm): 9.85 (s, 1H, OH); 4.61 (d, 1H, J=15.4 Hz, CO—CH$_2$—O); 4.19 (d, 1H, J=15.4 Hz, CO—CH$_2$—O); 4.16-4.07 (m, 2H, O—CH$_2$); 3.62-3.58 (m, 1H, P—CH—O); 3.31 (t, 2H, J=7.8 Hz, CH$_2$—N); 3.11 (t, 2H, J=7.8 Hz, CH$_2$—N); 1.96-1.74 (m, 2H, CH$_2$—CH—P); 1.70-1.60 (m, 2H, O—CH$_2$—CH$_2$); 1.59-1.47 (m, 4H, CH$_2$—CH$_2$—N); 1.45-1.35 (m, 2H, O—CH$_2$—CH$_2$—CH$_2$); 1.34-1.20 (m, 32H, CH$_2$); 0.94-0.86 (m, 12H, CH$_3$)

$^{31}$P NMR (160 MHz, CDCl$_3$) δ (ppm): 22.1

HRMS (EI+): calculated for C$_{31}$H$_{64}$NO$_5$P: 562.4600; found: 562.4604

6.4 Synthesis of butyl (((N,N-diethylhexylcarbamoyl)-2-oxoethoxy)ethyl)-phosphonate The synthesis of butyl (((N,N-diethyllhexylcarbamoyl)-2-oxoethoxy)ethyl)-phosphonate is obtained by the reaction of the alcohol-phosphonate in which R$_5$=R$_6$=n-C$_4$H$_9$O (BuO) and R$_1$=CH$_3$ (see paragraph 4.2 above), with the halide-amide in which X=Cl, R$_7$=R$_8$=n-C$_8$H$_{17}$ (Oct) and R$_2$=H.

The corresponding reaction, noted (14), is the following:

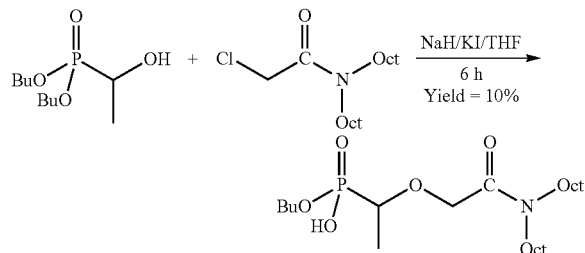

The characterisation data of this amido-phosphonate, synthesised with a 10% yield, are the following:

$^1$H NMR (400 MHz, CDCl$_3$) δ (ppm): 4.48 (d, 1H, J=16 Hz, CO—CH$_2$—O); 4.19 (d, 1H, J=15.4 Hz, CO—CH$_2$—O); 4.21-4.10 (m, 3H, CO—CH$_2$—O and O—CH$_2$); 3.77-3.71 (m, 1H, P—CH—O); 3.33 (t, 2H, J=7.6 Hz, CH$_2$—N); 3.10 (t, 2H, J=7.6 Hz, CH$_2$—N); 1.73-1.65 (m, 2H, O—CH$_2$—CH$_2$); 1.60-1.38 (m, 9H, CH$_2$—CH$_2$—N and O—CH$_2$—CH$_2$—CH$_2$ and CH$_3$—CH); 1.37-1.21 (m, 20H, CH$_2$); 0.97-0.87 (m, 9H, CH$_3$)

$^{31}$P NMR (160 MHz, CDCl$_3$) δ (ppm): 22.3

HRMS (EI+): calculated for C$_{24}$H$_{50}$NO$_5$P: 463.3505; found: 463.3507

6.5 Synthesis of butyl (((N,N-diethylhexylcarbamoyl)-1-oxopropan-2-yl)methyl)-phosphonate The synthesis of butyl (((N,N-diethylhexylca rbamoyl)-1-oxopropan-2-yl)methyl)-phosphonate is obtained by the reaction of the alcohol-phosphonate in which R$_5$=R$_6$=n-C$_4$H$_9$O (BuO) and R$_1$=H (see paragraph 2.1 above), with the halide-amide in which X=Br, R$_7$=R$_3$=n-C$_3$H$_{17}$ (Oct) and R$_2$=CH$_3$.

The corresponding reaction, noted (15), is the following:

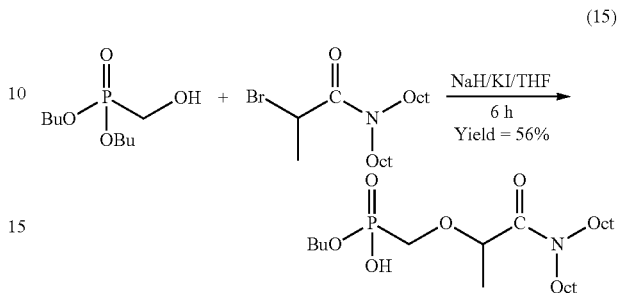

The characterisation data of this amido-phosphonate, synthesised with a 56% yield, are the following:

$^1$H NMR (400 MHz, CDCl$_3$) δ (ppm): 10.6 (s, 1H, OH); 4.47-4.42 (m, 1H, CH); 4.14-4.08 (m, 2H, O—CH$_2$); 3.76 (dd, 2H, J=8.8 and 3.8 Hz, P—CH$_2$—O); 3.49-3.41 (m, 1H, CH$_2$—N); 3.30-3.16 (m, 3H, CH$_2$—N); 1.71-1.64 (m, 2H, O—CH$_2$—CH$_2$); 1.61-1.48 (m, 4H, CH$_2$—CH$_2$—N); 1.47-1.37 (m, 5H, O—CH$_2$—CH$_2$—CH$_2$ and CH$_3$—CH); 1.34-1.24 (m, 20H, CH$_2$); 0.96-0.86 (m, 9H, CH$_3$)

$^{31}$P NMR (160 MHz, CDCl$_3$) δ (ppm): 21.8

HRMS (EI+): calculated for C$_{24}$H$_{50}$NO$_5$P: 463.3505; found: 463.3507

6.6 Synthesis of ethylhexyl (((N,N-dioctylcarbamoyl)-2-oxoethoxy)methyl)-phosphonate The synthesis of ethylhexyl (((N,N-dioctylcarbamoyl)-2-oxoethoxy)methyl)-phosphonate is obtained by the reaction of the alcohol-phosphonate in which R$_5$=R$_6$=2-ethylhexyl (noted EtHex or HexEt) and R$_1$=H (see paragraph 4.3 above), with the halide-amide in which X=Cl, R$_7$=R$_8$=n-C$_3$H$_{17}$ (Oct) and R$_2$=H.

The corresponding reaction, noted (16), is the following:

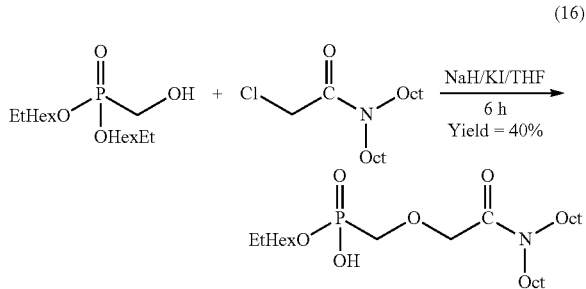

The characterisation data of this amido-phosphonate, synthesised with a 40% yield, are the following:

$^1$H NMR (400 MHz, CDCl$_3$) δ (ppm): 10.4 (s, 1H, OH); 4.35 (s, 2H, CO—CH$_2$—O); 4.08-3.98 (m, 2H, O—CH$_2$); 3.96 (d, 2H, J=8 Hz, P—CH$_2$—O); 3.32 (t, 2H, J=7.6 Hz, CH$_2$—N); 3.12 (t, 2H, J=7.6 Hz, CH$_2$—N); 1.63-1.49 (m, 5H, CH$_2$—CH$_2$—N and CH); 1.48-1.23 (m, 28H, CH$_2$); 0.92-0.88 (m, 12H, CH$_3$)

$^{31}$P NMR (160 MHz, CDCl$_3$) δ (ppm): 21.2

HRMS (EI+): calculated for C$_{27}$H$_{56}$NO$_4$P: 489.4025; found: 489.4024

Example 7: Synthesis of an Amido-Phosphinate

The synthesis of an amido-phosphinate implements an alcohol-phosphinate with a halide-amide, according to the Williamson reaction, in the presence of sodium hydride (NaH) and potassium iodide (KI) in tetrahydrofuran (THF).

The corresponding reaction, noted (10bis), is the following, it being specified that the alkoxyl group among $R_5$ and $R_6$ hydrolyses during this reaction:

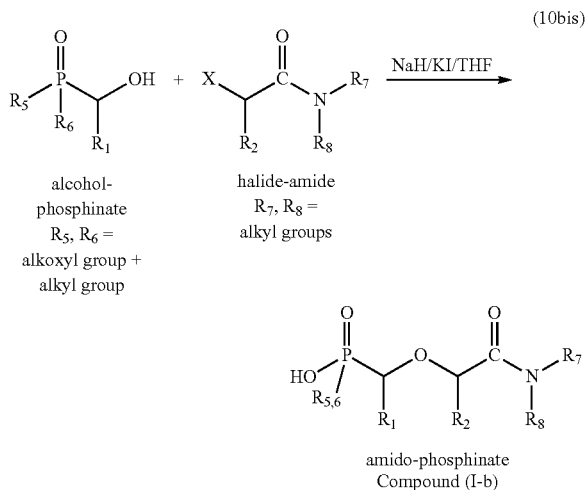

The present reaction is illustrated with the synthesis of octyl (((N,N-dioctylcarbamoyl)-2-oxoethoxy)methyl)-phosphinate which is obtained by the reaction of the alcohol-phosphinate in which $R_5$ (or $R_6$)=n-$C_3H_{17}$ (Oct), $R_6$ (or $R_5$)=$C_2H_5O$ (EtO) and $R_1$=H (see example 5 above), with the halide-amide in which X=Cl, $R_7$=$R_8$=n-$C_8H_{17}$ (Oct) and $R_2$=H.

It is specified that this synthesis is carried out according to the operating protocol described above, in chapter 6, for the synthesis of amido-phosphonates, the solution of alcohol-phosphonate in THF being, in the present case, replaced by a solution) of alcohol-phosphinate.

The corresponding reaction, noted (17), is the following:

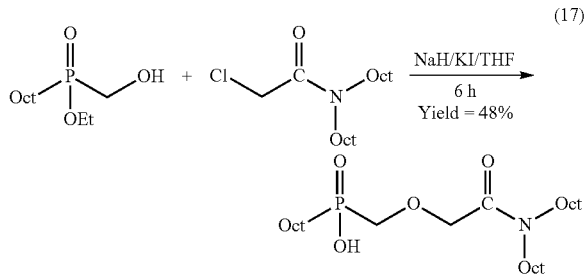

The characterisation data of this amido-phosphonate, synthesised with a 48% yield, are the following:

$^1$H NMR (400 MHz, CDCl$_3$) δ (ppm): 4.34 (s, 2H, CO—CH$_2$—O); 3.88 (d, 2H, J=6 Hz, P—CH$_2$—O); 3.32 (t, 2H, J=7.8 Hz, CH$_2$—N); 3.12 (t, 2H, J 7, Hz, CH$_2$—N); 1.88-1.80 (m, 2H, CH$_2$—P); 1.72-1.62 (m, 2H, CH$_2$—CH$_2$—P); 1.61-1.49 (m, 4H, CH$_2$—CH$_2$—N); 1.44-1.20 (m, 28H, CH$_2$); 0.93-0.88 (m, 9H, CH$_3$)

$^{31}$P NMR (160 MHz, CDCl$_3$) δ (ppm): 48.6

HRMS (EI+): calculated for $C_{27}H_{56}NO_4P$: 489.4025; found: 489.4024

Extracting Properties of Compounds According to the Invention

Modalities For Evaluating Extracting Properties

The extracting properties of the compounds were evaluated by measuring the distribution coefficients of the species in solution, by Inductively Coupled Plasma-Optic Emission Spectrometry (ICP-OES), after dilution of the aqueous solutions to measurable contents (between 0 and 20 ppm), before and after contact with the organic phase.

* Unless stated otherwise or a third phase appears at the extraction, the distribution coefficient of a metal element M, noted $D_M$, between an organic phase and) an aqueous phase is determined by the following equation:

$$D_M = \frac{[M]_{org.}}{[M]_{aq.}}$$

with $[M]_{org.}$=concentration of the metal element in the organic phase at the extraction equilibrium (in Mg/L), and $[M]_{aq.}$=concentration of the metal element in the aqueous phase at the extraction equilibrium (in Mg/L).

* The selectivity of the extraction is systematically evaluated from the selectivity factor, noted FS and determined by the following equation:

$$FS = \frac{D_{M1}}{D_{M2}}$$

with $D_{M1}$=distribution coefficient of the metal element M1, and $D_{M2}$=distribution coefficient of the metal element M2 (iron will mainly be considered).

* The extraction performance is expressed by the extraction percentage, noted E(%) and determined by the following equation:

$$E(\%) = \frac{D_M}{D_M + \left(\frac{A}{O}\right)} \times 100$$

with $D_M$=distribution coefficient of the metal element M, and

A/O=ratio between the volumes of the aqueous and organic phases.

Operating Protocols

In order to be as close as possible to the conditions encountered during extractions of lixiviation liquors, the extraction tests were carried out with acid aqueous phases comprising several metal elements, noted M, and organic phases comprising an extraction agent. More precisely, these metal elements M comprise a transition metal (Fe) as well as lanthanides, noted Ln, totalling 5 in number (La, Nd, Gd, Dy and Yb).

The compositions of the aqueous and organic phases, before contact, are the following, it being specified that the unit "M" used here and hereafter corresponds to the abbreviation of the SI unit "mol/L":

Aqueous Phases:
  1 mM of each of the lanthanides La, Nd, Gd, Dy and Yb, and 50 mM of Fe,
  from 0.5 M to 5 M of $H_3PO_4$ with, optionally, a modification of the ionic force by addition of 0.1 M to 2 M of $NaNO_3$.
Organic Phases:
  from 10 mM to 100 mM of extraction agent in dodecane, it being noted that the molar concentration of extraction agent is at least equal to two times the total molar concentration of lanthanides.

Each aqueous solution is brought into contact with an organic solution comprising the considered extraction agent in dodecane.

This bringing into contact is carried out volume by volume (that is to say that the volumes of organic solution Vorg and of aqueous solution Vaq are identical, Vorg=Vaq), by mechanical stirring, for 20 minutes, in a 15 mL tube and at room temperature (21-22° C.). After centrifugation, the resulting aqueous and organic phases are separated from each other then are each analysed by ICP-OES.

Experimental Results

Example 8: Extraction by TODGA (Comparative Example)

The present example was carried out in the following conditions:
Aqueous phase: 1 mM of each lanthanide (La, Nd, Gd, Dy, Yb)+50 mM of Fe in variable concentrations of phosphoric acid ([$H_3PO_4$]=from 0.5 M to 5 M)
Organic phase: 10 mM of extraction agent in dodecane, the extraction agent being TODGA of formula (extraction agent described in reference [1]):

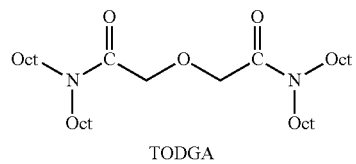

TODGA

The calculated values of the distribution coefficients D and the extraction percentages E(%) are reported in table 1 below:

TABLE 1

| | [$H_3PO_4$] (in M) | | | | | | | |
|---|---|---|---|---|---|---|---|---|
| | 5 | | 3 | | 1 | | 0.5 | |
| Element M | | | | | | | | |
| | D | E(%) | D | E(%) | D | E(%) | D | E(%) |
| Fe | <0.001 | <0.1 | <0.001 | <0.1 | <0.001 | <0.1 | <0.001 | <0.1 |
| La | <0.001 | <0.1 | <0.01 | <1 | <0.01 | <1 | <0.01 | <1 |
| Nd | <0.001 | <0.1 | <0.01 | <1 | <0.01 | <1 | <0.01 | <1 |
| Gd | 0.01 | 1 | 0.01 | 1 | <0.02 | <2 | <0.02 | <2 |
| Dy | 0.01 | 1 | 0.01 | 1 | <0.02 | <2 | <0.02 | <2 |
| Yb | 0.01 | 1 | 0.01 | 1 | <0.02 | <2 | <0.02 | <2 |

As reported in table 1 above, the values of the extraction percentages E(%) as obtained are all below 2% and this applies whatever the concentration of phosphoric acid in the aqueous phase.

These results clearly highlight the fact that TOGDA absolutely does not make it possible to extract lanthanides from an aqueous phase comprising phosphoric acid, unlike what happens when the aqueous phase comprises nitric acid (see reference [1]).

Example 9: Extraction by a Phosphonate-Phosphine Oxide

The present example was carried out in the following conditions:
Aqueous phase: 1 mM of each lanthanide (La, Nd, Gd, Dy, Yb)+50 mM of Fe in variable concentrations of phosphoric acid ([$H_3PO_4$]=from 0.5 M to 5 M)
Organic phase: 10 mM of extraction agent in dodecane, the extraction agent being the following compound (see paragraph 2.3 above):

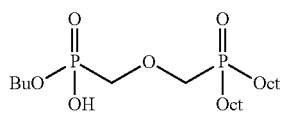

The calculated values of the distribution coefficients D and the extraction percentages E(%) are reported in table 2.1 below:

TABLE 2.1

| | [$H_3PO_4$] (in M) | | | | | | | |
|---|---|---|---|---|---|---|---|---|
| | 5 | | 3 | | 1 | | 0.5 | |
| Element M | | | | | | | | |
| | D | E(%) | D | E(%) | D | E(%) | D | E(%) |
| Fe | 0.004 | 0.4 | 0.21 | 17 | 0.47 | 32 | 0.65 | 24 |
| La | <0.001 | <0.1 | 0.03 | 3 | 0.03 | 3 | 0.06 | 6 |
| Nd | <0.001 | <0.1 | 0.02 | 2 | 0.05 | 4 | 0.2 | 15 |
| Gd | <0.001 | <0.1 | 0.02 | 2 | 0.05 | 5 | 0.15 | 13 |
| Dy | 0.15 | 13 | 0.06 | 6 | 0.12 | 11 | 0.29 | 22 |
| Yb | 0.63 | 39 | 2.56 | 72 | 6.8 | 87 | 10.4 | 91 |

The calculated values of the selectivity factors FS of each lanthanide Ln compared to Fe, noted $FS_{Ln/Fe}$, are reported in table 2.2 below:

TABLE 2.2

| | [$H_3PO_4$] (in M) | | | |
|---|---|---|---|---|
| | 5 | 3 | 1 | 0.5 |
| Lanthanide Ln | | | | |
| | $FS_{Ln/Fe}$ | $FS_{Ln/Fe}$ | $FS_{Ln/Fe}$ | $FS_{Ln/Fe}$ |
| La | <0.25 | 0.14 | 0.06 | 0.09 |
| Nd | <0.25 | 0.10 | 0.11 | 0.26 |
| Gd | <0.25 | 0.10 | 0.11 | 0.23 |
| Dy | 2.5 | 0.29 | 0.26 | 0.45 |
| Yb | 158 | 12 | 14 | 16 |

The calculated values of the selectivity factors FS of the element Yb compared to each element M, noted $FS_{Yb/M}$, are reported in table 2.3 below:

TABLE 2.3

| | [H$_3$PO$_4$] (in M) | | | |
| | 5 | 3 | 1 | 0.5 |
| Element M | | | | |
| | FS$_{Yb/M}$ | FS$_{Yb/M}$ | FS$_{Yb/M}$ | FS$_{Yb/M}$ |
|---|---|---|---|---|
| Fe | 158 | 12 | 14 | 16 |
| La | >200 | 85 | >200 | 173 |
| Nd | >200 | 128 | 136 | 52 |
| Gd | >200 | 128 | 136 | 69 |
| Dy | 63 | 43 | 57 | 36 |

The extraction agent used in the present example is efficient for the extraction of Yb in phosphoric medium, quite particularly at 0.5 M.

Although the Yb extraction performance is lower at 5 M [H$_3$PO$_4$] (39%), this extraction is, on the other hand, particularly selective with respect to other lanthanides (FS$_{Yb/Dy}$>60 and FS$_{Yb/Ln}$>200 for Ln=La, Nd, Gd) as well as with respect to iron (FS$_{Yb/Fe}$=158) at such a molar concentration.

The Yb extraction performance is enhanced for lower acidities (for example, E(%)=91% at 0.5 M in [H$_3$PO$_4$]), but a reduction in the selectivity factor with respect to iron (FS$_{Yb/Fe}$=16 at 0.5 M in [H$_3$PO$_4$]) is then observed.

Example 10: Extraction by an Amido-Phosphinate

The present example was carried out in the following conditions:
Aqueous phase: 1 mM of each lanthanide (La, Nd, Gd, Dy, Yb)+50 mM of Fe in variable concentrations of phosphoric acid ([H$_3$PO$_4$]=from 0.5 M to 5 M)
Organic phase: 10 mM of extraction agent in dodecane, the extraction agent being the following compound (see example 7 above):

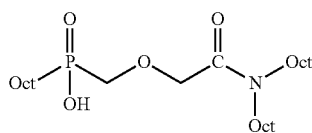

The calculated values of the distribution coefficients D and the extraction percentages E(%) are reported in table 3.1 below:

TABLE 3.1

| | [H$_3$PO$_4$] (in M) | | | | | | | |
| | 5 | | 3 | | 1 | | 0.5 | |
| Element M | | | | | | | | |
| | D | E(%) | D | E(%) | D | E(%) | D | E(%) |
|---|---|---|---|---|---|---|---|---|
| Fe | 0.001 | 0.1 | 0.24 | 19 | 0.54 | 35 | 0.51 | 34 |
| La | 0.01 | 1 | 0.02 | 2 | 0.02 | 2 | 0.07 | 7 |
| Nd | 0.03 | 3 | 0.02 | 2 | 0.03 | 3 | 0.17 | 15 |
| Gd | 0.04 | 4 | 0.03 | 3 | 0.02 | 2 | 0.25 | 20 |
| Dy | 0.07 | 7 | 0.04 | 4 | 0.02 | 2 | 0.25 | 20 |
| Yb | 0.11 | 10 | 0.20 | 17 | 0.23 | 19 | 1.52 | 60 |

The calculated values of the selectivity factors FS of each lanthanide Ln compared to Fe, noted FS$_{Ln/Fe}$, are reported in table 3.2 below:

TABLE 3.2

| | [H$_3$PO$_4$] (in M) | | | |
| | 5 | 3 | 1 | 0.5 |
| Lanthanide Ln | | | | |
| | FS$_{Ln/Fe}$ | FS$_{Ln/Fe}$ | FS$_{Ln/Fe}$ | FS$_{Ln/Fe}$ |
|---|---|---|---|---|
| La | 10 | 0.08 | 0.04 | 0.14 |
| Nd | 30 | 0.08 | 0.06 | 0.33 |
| Gd | 40 | 0.13 | 0.04 | 0.49 |
| Dy | 70 | 0.17 | 0.04 | 0.49 |
| Yb | 110 | 0.83 | 0.43 | 2.98 |

The extraction agent used in the present example is efficient for the extraction of Yb in 0.5 M phosphoric medium, with E(%)=60%, it being noted that, at this molar concentration of [H$_3$PO$_4$], the selectivity with respect to iron is lower (FS$_{Yb/Fe}$=2.98).

Example 11: Extraction by a First Amido-Phosphonate

In this example 11, the extraction agent used is the following compound (see paragraph 6.1 above):

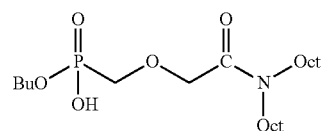

11.1 A first series of extractions was carried out in the following conditions:
Aqueous phase: 1 mM of each lanthanide (La, Nd, Gd, Dy, Yb)+50 mM of Fe in variable concentrations of phosphoric acid ([H$_3$PO$_4$]=from 0.5 M to 5 M)
Organic phase: 10 mM of the above extraction agent in dodecane The calculated values of the distribution coefficients D and the extraction percentages E(%) are reported in table 4.1 below:

TABLE 4.1

| | [H$_3$PO$_4$] (in M) | | | | | | | |
| | 5 | | 3 | | 1 | | 0.5 | |
| Element M | | | | | | | | |
| | D | E(%) | D | E(%) | D | E(%) | D | E(%) |
|---|---|---|---|---|---|---|---|---|
| Fe | 0.02 | 1.5 | 0.04 | 4 | 0.18 | 15 | 0.21 | 17 |
| La | <0.001 | <0.1 | <0.001 | <0.1 | <0.001 | <0.1 | <0.001 | <0.1 |
| Nd | 0.9 | 47 | 0.5 | 33 | 0.28 | 22 | 0.35 | 26 |
| Gd | 6.5 | 87 | 2.89 | 74 | 0.67 | 40 | 0.68 | 40 |
| Dy | 28.5 | 97 | 11.7 | 92 | 1.35 | 57 | 1.17 | 54 |
| Yb | 81 | 99 | 69.5 | 99 | 5.97 | 86 | 3.64 | 78 |

The calculated values of the selectivity factors FS of each lanthanide Ln compared to Fe, noted FS$_{Ln/Fe}$, are reported in table 4.2 below:

TABLE 4.2

| | [H₃PO₄] (in M) | | | |
|---|---|---|---|---|
| | 5 | 3 | 1 | 0.5 |
| Lanthanide Ln | | | | |
| | $FS_{Ln/Fe}$ | $FS_{Ln/Fe}$ | $FS_{Ln/Fe}$ | $FS_{Ln/Fe}$ |
| La | <0.1 | <0.1 | <0.1 | <0.1 |
| Nd | 60 | 13 | 2 | 2 |
| Gd | >200 | 74 | 4 | 3 |
| Dy | >>200 | >200 | 8 | 6 |
| Yb | >>200 | >>200 | 34 | 14 |

11.2 A second series of extractions was carried out in the following conditions:
Aqueous phase: 1 mM of each lanthanide (La, Nd, Gd, Dy, Yb)+50 mM of Fe in phosphoric acid ([H₃PO₄]=5 M)
Organic phase: variable concentrations of extraction agent ([extraction agent]=from 10 mM to 40 mM) in dodecane
The calculated values of the distribution coefficients D and the extraction percentages E(%) are reported in table 4.3 below:

The extraction agent used in the present example is efficient for the extraction of all the lanthanides tested (with the exception of La), with a more pronounced performance for lanthanides with the highest atomic numbers (Dy and Yb).

This extraction agent also makes it possible to attain good selectivity with respect to iron ($FS_{Nd/Fe}$=60 and $FS_{Ln/Fe}$ greater (>), or even much greater (>>), than 200 for Ln=Gd, Dy, Yb), in 5 M and 3 M phosphoric medium.

The increase in the molar concentration of this extraction agent as well as the addition of NaNO₃ make it possible to increase the extraction performance of all the lanthanides, notably of lanthanides of lower atomic number (La and Nd), while conserving good separation factors with respect to iron.

TABLE 4.3

| | [extraction agent] (mM) | | | | | | | | | | | | | |
|---|---|---|---|---|---|---|---|---|---|---|---|---|---|---|
| | 10 | | 15 | | 20 | | 25 | | 30 | | 35 | | 40 | |
| Element M | | | | | | | | | | | | | | |
| | D | E(%) | D | E(%) | D | E(%) | D | E(%) | D | E(%) | D | E(%) | D | E(%) |
| Fe | 0.02 | 1.5 | 0.001 | 0.1 | 0.04 | 4 | 0.06 | 6 | 0.07 | 7 | 0.12 | 11 | 0.41 | 29 |
| La | <0.001 | <0.1 | 0.2 | 17 | 0.34 | 25 | 0.49 | 33 | 0.69 | 41 | 1.1 | 52 | 5.2 | 84 |
| Nd | 0.9 | 47 | 2 | 67 | 2.9 | 74 | 3.7 | 79 | 4.5 | 82 | 6.2 | 86 | 24 | 96 |
| Gd | 6.5 | 87 | 15 | 94 | 19 | 95 | 22 | 96 | 23 | 96 | 26 | 96 | 51.5 | 98 |
| Dy | 28.5 | 97 | 48 | 98 | 59 | 98 | 67 | 99 | 70 | 99 | 75 | 99 | 94 | 99 |
| Yb | 81 | 99 | >500 | ≥99.9 | >500 | ≥99.9 | >500 | ≥99.9 | >500 | ≥99.9 | >500 | ≥99.9 | >500 | ≥99.9 |

11.3 A third series of extractions was carried out in the following conditions:
Aqueous phase: 1 mM of each lanthanide (La, Nd, Gd, Dy, Yb)+50 mM of Fe in phosphoric acid ([H₃PO₄]=5 M), optionally with added sodium nitrate ([NaNO₃]=from 0 to 2 M)
Organic phase: 15 mM of the above extraction agent in dodecane
The calculated values of the distribution coefficients D and the extraction percentages E(%) are reported in table 4.4 below:

Example 12: Extraction by a Second Amido-Phosphonate

In this example 12, the extraction agent used is the following compound (see paragraph 6.6 above):

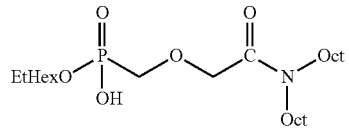

TABLE 4.4

| | [NaNO₃] (M) | | | | | | | | | |
|---|---|---|---|---|---|---|---|---|---|---|
| | 0 | | 0.1 | | 0.5 | | 1 | | 2 | |
| Element M | | | | | | | | | | |
| | D | E(%) | D | E(%) | D | E(%) | D | E(%) | D | E(%) |
| Fe | 0.001 | 0.1 | 0.01 | 0.1 | 0.04 | 4 | 0.06 | 6 | 0.07 | 7 |
| La | 0.2 | 17 | 0.19 | 16 | 0.41 | 29 | 0.51 | 34 | 0.57 | 36 |
| Nd | 2 | 67 | 3 | 73 | 6 | 86 | 7 | 88 | 7 | 87 |
| Gd | 15 | 94 | 25 | 96 | 72 | 99 | 105 | 99 | 111 | 99 |
| Dy | 48 | 98 | 97 | 98 | 331 | 99.7 | 535 | 99.8 | >500 | ≥99.9 |
| Yb | >500 | ≥99.9 | >500 | ≥99.9 | >500 | ≥99.9 | >500 | ≥99.9 | >500 | ≥99.9 |

12.1 A first series of extractions was carried out in the following conditions:

Aqueous phase: 1 mM of each lanthanide (La, Nd, Gd, Dy, Yb)+50 mM of Fe in variable concentrations of phosphoric acid ($[H_3PO_4]$=from 0.5 M to 5 M)

Organic phase: 10 mM of the above extraction agent in dodecane

The calculated values of the distribution coefficients D and the extraction percentages E(%) are reported in table 5.1 below:

TABLE 5.1

| | $[H_3PO_4]$ (in M) | | | | | | | |
|---|---|---|---|---|---|---|---|---|
| | 5 | | 3 | | 1 | | 0.5 | |
| | Element M | | | | | | | |
| | D | E(%) | D | E(%) | D | E(%) | D | E(%) |
| Fe | 0.03 | 3 | 0.01 | 1 | 0.26 | 20 | 0.36 | 26.5 |
| La | <0.001 | <0.1 | <0.001 | <0.1 | <0.001 | <0.1 | <0.001 | <0.1 |
| Nd | 0.07 | 6.5 | 0.1 | 9 | 0.03 | 3 | 0.01 | 1 |
| Gd | 0.08 | 7 | 0.1 | 9 | 0.04 | 4 | 0.01 | 1 |
| Dy | 0.14 | 12 | 0.2 | 17 | 0.11 | 10 | 0.07 | 6.5 |
| Yb | 0.26 | 21 | 0.72 | 42 | 1.40 | 58 | 1.67 | 62.5 |

The calculated values of the selectivity factors FS of each lanthanide Ln compared to Fe, noted $FS_{Ln/Fe}$, are reported in table 5.2 below:

TABLE 5.2

| | $[H_3PO_4]$ (in M) | | | |
|---|---|---|---|---|
| | 5 | 3 | 1 | 0.5 |
| | Lanthanide Ln | | | |
| | $FS_{Ln/Fe}$ | $FS_{Ln/Fe}$ | $FS_{Ln/Fe}$ | $FS_{Ln/Fe}$ |
| La | <0.1 | <0.1 | <0.1 | <0.1 |
| Nd | 2 | 2 | 8 | 0.1 |
| Gd | 3 | 8 | 0.1 | <0.1 |
| Dy | 5 | 17 | 0.4 | 0.2 |
| Yb | 9 | 61 | 5.5 | 5 |

12.2 A second series of extractions was carried out in the following conditions:

Aqueous phase: 1 mM of each lanthanide (La, Nd, Gd, Dy, Yb)+50 mM of Fe in phosphoric acid ($[H_3PO_4]$=5 M)

Organic phase: variable concentrations of extraction agent ([extraction agent]=from 10 mM to 40 mM) in dodecane The calculated values of the distribution coefficients D and the extraction percentages E(%) are reported in table 5.3 below:

TABLE 5.3

| | [extractant] (mM) | | | | | | | | | | | | | |
|---|---|---|---|---|---|---|---|---|---|---|---|---|---|---|
| | 10 | | 15 | | 20 | | 25 | | 30 | | 35 | | 40 | |
| | Element M | | | | | | | | | | | | | |
| | D | E(%) | D | E(%) | D | E(%) | D | E(%) | D | E(%) | D | E(%) | D | E(%) |
| Fe | 0.03 | 3 | 0.03 | 3 | 0.07 | 6.5 | 0.005 | 0.5 | 0.17 | 14.5 | 0.22 | 18 | 0.25 | 20 |
| La | <0.001 | <0.1 | 0.11 | 10 | 0.17 | 14.5 | 0.23 | 19 | 0.32 | 24 | 0.37 | 27 | 0.44 | 31 |
| Nd | 0.07 | 6.5 | 0.28 | 22 | 0.41 | 29 | 0.56 | 36 | 0.78 | 44 | 0.94 | 48.5 | 1.1 | 53 |
| Gd | 0.08 | 7 | 0.32 | 24 | 0.45 | 31 | 0.61 | 38 | 0.85 | 46 | 1 | 51 | 1.3 | 56 |
| Dy | 0.14 | 12 | 0.47 | 32 | 0.68 | 40.5 | 0.95 | 49 | 1.3 | 56.5 | 1.6 | 61 | 2 | 66 |
| Yb | 0.26 | 21 | 2.5 | 71 | 3.2 | 76 | 4 | 80 | 5 | 83 | 6 | 85 | 7 | 87 |

12.3 A third series of extractions was carried out in the following conditions:

Aqueous phase: 1 mM of each lanthanide (La, Nd, Gd, Dy, Yb)+50 mM of Fe in phosphoric acid ($[H_3PO_4]$=5 M), optionally with added sodium nitrate ($[NaNO_3]$=from 0 to 2 M)

Organic phase: 15 mM of the above extraction agent in dodecane

The calculated values of the distribution coefficients D and the extraction percentages E(%) are reported in table 5.4 below:

TABLE 5.4

| | $[NaNO_3]$ (M) | | | | | | | | | |
|---|---|---|---|---|---|---|---|---|---|---|
| | 0 | | 0.1 | | 0.5 | | 1 | | 2 | |
| | Element M | | | | | | | | | |
| | D | E(%) | D | E(%) | D | E(%) | D | E(%) | D | E(%) |
| Fe | 0.03 | 3 | 0.004 | 0.4 | <0.001 | <0.1 | <0.001 | <0.1 | <0.001 | <0.1 |
| La | 0.11 | 10 | 0.07 | 7 | 0.11 | 10 | 0.16 | 14 | 0.17 | 15 |
| Nd | 0.28 | 22 | 0.18 | 15 | 0.4 | 29 | 0.55 | 35 | 0.67 | 40 |
| Gd | 0.32 | 24 | 0.23 | 19 | 0.6 | 38 | 1 | 50 | 1.5 | 61 |
| Dy | 0.47 | 32 | 0.35 | 26 | 0.82 | 45 | 1.3 | 57 | 2 | 66 |
| Yb | 2.5 | 71 | 0.6 | 36 | 0.9 | 47 | 1.1 | 53 | 1.5 | 59 |

The extraction agent used in the present example remains efficient for the extraction of Yb in phosphoric medium, this extraction performance being inversely proportional to the molar concentration of [$H_3PO_4$].

As in example 11, it is observed that the increase in the molar concentration of this extraction agent as well as the addition of $NaNO_3$ make it possible to increase the extraction performance of all the lanthanides, notably of lanthanides of lower atomic number (La and Nd), while conserving good separation factors with respect to iron.

Example 13: Extraction by a Third Amido-Phosphonate

In this example 13, the extraction agent used is the following compound (see paragraph 6.3 above):

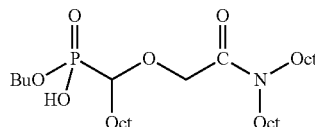

13.1 A first series of extractions was carried out in the following conditions:

Aqueous phase: 1 mM of each lanthanide (La, Nd, Gd, Dy, Yb)+50 mM of Fe in variable concentrations of phosphoric acid ([$H_3PO_4$]=from 0.5 M to 5 M)

Organic phase: 10 mM of the above extraction agent in dodecane

The calculated values of the distribution coefficients D and the extraction percentages E(%) are reported in table 6.1 below:

TABLE 6.1

| | [$H_3PO_4$] (in M) | | | | | | | |
|---|---|---|---|---|---|---|---|---|
| | 5 | | 3 | | 1 | | 0.5 | |
| Element M | | | | | | | | |
| | D | E(%) | D | E(%) | D | E(%) | D | E(%) |
| Fe | 0.03 | 3 | <0.001 | <0.1 | 0.13 | 20 | 0.26 | 26.5 |
| La | <0.001 | <0.1 | <0.001 | <0.1 | <0.001 | <0.1 | <0.001 | <0.1 |
| Nd | <0.001 | <0.1 | <0.001 | <0.1 | <0.001 | <0.1 | <0.001 | <0.1 |
| Gd | <0.001 | <0.1 | <0.001 | <0.1 | <0.001 | <0.1 | <0.001 | <0.1 |
| Dy | 0.02 | 2 | 0.02 | 2 | 0.07 | 6.5 | 0.09 | 8 |
| Yb | 0.16 | 14 | 0.5 | 33 | 2 | 66 | 2.4 | 71 |

The calculated values of the selectivity factors FS of each lanthanide Ln compared to Fe, noted $FS_{Ln/Fe}$, are reported in table 6.2 below:

TABLE 6.2

| | [$H_3PO_4$] (in M) | | | |
|---|---|---|---|---|
| | 5 | 3 | 1 | 0.5 |
| Lanthanide Ln | | | | |
| | $FS_{Ln/Fe}$ | $FS_{Ln/Fe}$ | $FS_{Ln/Fe}$ | $FS_{Ln/Fe}$ |
| La | <0.1 | 10 | <0.1 | <0.1 |
| Nd | <0.1 | 10 | <0.1 | <0.1 |
| Gd | <0.1 | 10 | <0.1 | <0.1 |
| Dy | 0.7 | 200 | 0.5 | 0.3 |
| Yb | 5.5 | >>200 | 15 | 9.5 |

The calculated values of the selectivity factors FS of the element Yb compared to each element M, noted $FS_{Yb/M}$, are reported in table 6.3 below:

TABLE 6.3

| | [$H_3PO_4$] (in M) | | | |
|---|---|---|---|---|
| | 5 | 3 | 1 | 0.5 |
| Element M | | | | |
| | $FS_{Yb/M}$ | $FS_{Yb/M}$ | $FS_{Yb/M}$ | $FS_{Yb/M}$ |
| Fe | 5.5 | >>200 | 15 | 9.5 |
| La | >150 | >>200 | >>200 | >>200 |
| Nd | >150 | >>200 | >>200 | >>200 |
| Gd | >150 | >>200 | >>200 | >>200 |
| Dy | 8 | 25 | 28 | 27 |

13.2 A second series of extractions was carried out in the following conditions:

Aqueous phase: 1 mM of each lanthanide (La, Nd, Gd, Dy, Yb)+50 mM of Fe in phosphoric acid ([$H_3PO_4$]=5 M)

Organic phase: variable concentrations of extraction agent ([extraction agent]=10 mM to 40 mM) in dodecane The calculated values of the distribution coefficients D and the extraction percentages E(%) are reported in table 6.4 below:

TABLE 6.4

| | [extraction agent] (mM) | | | | | | | | | | | | | |
|---|---|---|---|---|---|---|---|---|---|---|---|---|---|---|
| | 10 | | 15 | | 20 | | 25 | | 30 | | 35 | | 40 | |
| Element M | | | | | | | | | | | | | | |
| | D | E(%) | D | E(%) | D | E(%) | D | E(%) | D | E(%) | D | E(%) | D | E(%) |
| Fe | 0.03 | 3 | 0.002 | 0.2 | 0.02 | 2 | 0.04 | 4 | 0.08 | 7 | 0.12 | 11 | 0.18 | 15 |
| La | <0.001 | <0.1 | 0.01 | 1 | 0.02 | 2 | 0.03 | 3 | 0.04 | 4 | 0.05 | 5 | 0.06 | 6 |
| Nd | <0.001 | <0.1 | 0.06 | 6 | 0.07 | 6.5 | 0.1 | 9 | 0.12 | 11 | 0.14 | 12 | 0.16 | 14 |
| Gd | <0.001 | <0.1 | 0.08 | 7 | 0.08 | 7 | 0.11 | 10 | 0.12 | 11 | 0.14 | 12 | 0.16 | 14 |
| Dy | 0.02 | 2 | 0.11 | 10 | 0.13 | 11.5 | 0.19 | 16 | 0.23 | 19 | 0.27 | 21 | 0.32 | 24 |
| Yb | 0.16 | 14 | 2.3 | 69 | 3 | 75 | 4 | 79 | 5 | 83 | 6 | 86 | 7 | 88 |

Example 14: Extraction by a Fourth Amido-Phosphonate

The present example was carried out in the following conditions:

Aqueous phase: 1 mM of each lanthanide (La, Nd, Gd, Dy, Yb)+50 mM of Fe in variable concentrations of phosphoric acid ($[H_3PO_4]$=from 0.5 M to 5 M)

Organic phase: 10 mM of extraction agent in dodecane, the extraction agent being the following compound (see paragraph 6.4 above):

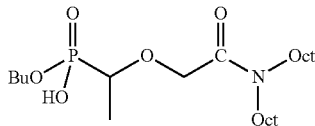

The calculated values of the distribution coefficients D and the extraction percentages E(%) are reported in table 7.1 below:

TABLE 7.1

| | [$H_3PO_4$] (in M) | | | | | | | |
|---|---|---|---|---|---|---|---|---|
| | 5 | | 3 | | 1 | | 0.5 | |
| | \multicolumn{8}{c}{Element M} |
| | D | E(%) | D | E(%) | D | E(%) | D | E(%) |
| Fe | 0.04 | 3.5 | 0.03 | 2.5 | 0.28 | 22 | 0.40 | 28 |
| La | <0.001 | 0.1< | <0.001 | <0.1 | <0.001 | <0.1 | <0.001 | <0.1 |
| Nd | <0.001 | 0.1< | <0.001 | <0.1 | <0.001 | <0.1 | <0.001 | <0.1 |
| Gd | <0.001 | 0.1< | <0.001 | <0.1 | <0.001 | <0.1 | <0.001 | <0.1 |
| Dy | 0.06 | 6 | 0.09 | 8 | 0.11 | 10 | 0.1 | 9 |
| Yb | 0.26 | 21 | 1 | 49 | 5.4 | 84 | 2.4 | 87 |

The calculated values of the selectivity factors FS of each lanthanide Ln compared to Fe, noted $FS_{Ln/Fe}$, are reported in table 7.2 below:

TABLE 7.2

| | [$H_3PO_4$] (in M) | | | |
|---|---|---|---|---|
| | 5 | 3 | 1 | 0.5 |
| | \multicolumn{4}{c}{Lanthanide Ln} |
| | $FS_{Ln/Fe}$ | $FS_{Ln/Fe}$ | $FS_{Ln/Fe}$ | $FS_{Ln/Fe}$ |
| La | <0.1 | <0.1 | <0.1 | <0.1 |
| Nd | <0.1 | <0.1 | <0.1 | <0.1 |
| Gd | <0.1 | <0.1 | <0.1 | <0.1 |
| Dy | 1.7 | 3.5 | 0.4 | 0.3 |
| Yb | 7 | 37 | 19 | 17.5 |

The calculated values of the selectivity factors FS of the element Yb compared to each element M, noted $FS_{Yb/M}$, are reported in table 7.3 below:

TABLE 7.3

| | [$H_3PO_4$] (in M) | | | |
|---|---|---|---|---|
| | 5 | 3 | 1 | 0.5 |
| | \multicolumn{4}{c}{Element M} |
| | $FS_{Yb/M}$ | $FS_{Yb/M}$ | $FS_{Yb/M}$ | $FS_{Yb/M}$ |
| Fe | 7 | 37 | 19 | 17.5 |
| La | >200 | >>200 | >>200 | >>200 |
| Nd | >200 | >>200 | >>200 | >>200 |
| Gd | >200 | >>200 | >>200 | >>200 |
| Dy | 4 | 11 | 49 | 69 |

Example 15: Extraction by a Fifth Amido-Phosphonate

The present example was carried out in the following conditions:

Aqueous phase: 1 mM of each lanthanide (La, Nd, Gd, Dy, Yb)+50 mM of Fe in variable concentrations of phosphoric acid ($[H_3PO_4]$=from 0.5 M to 5 M)

Organic phase: 10 mM of extraction agent in dodecane, the extraction agent being the following compound (see paragraph 6.5 above):

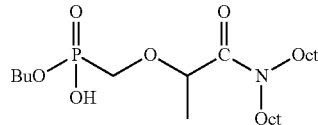

The calculated values of the distribution coefficients D and the extraction percentages E(%) are reported in table 8.1 below:

TABLE 8.1

| | [$H_3PO_4$] (in M) | | | | | | | |
|---|---|---|---|---|---|---|---|---|
| | 5 | | 3 | | 1 | | 0.5 | |
| | \multicolumn{8}{c}{Element M} |
| | D | E(%) | D | E(%) | D | E(%) | D | E(%) |
| Fe | 0.05 | 5 | 0.27 | 21 | 0.51 | 34 | 0.54 | 35 |
| La | <0.001 | <0.1 | <0.001 | <0.1 | <0.001 | <0.1 | <0.001 | <0.1 |
| Nd | <0.001 | <0.1 | <0.001 | <0.1 | <0.001 | <0.1 | <0.001 | <0.1 |
| Gd | <0.001 | <0.1 | <0.001 | <0.1 | <0.001 | <0.1 | <0.001 | <0.1 |
| Dy | 0.01 | 1 | 0.03 | 3 | 0.06 | 6 | 0.11 | 10 |
| Yb | 0.34 | 25 | 0.71 | 41.5 | 1.2 | 54 | 1.3 | 57 |

The calculated values of the selectivity factors FS of each lanthanide Ln compared to Fe, noted $FS_{Ln/Fe}$, are reported in table 8.2 below:

TABLE 8.2

| | [$H_3PO_4$] (in M) | | | |
|---|---|---|---|---|
| | 5 | 3 | 1 | 0.5 |
| | \multicolumn{4}{c}{Lanthanide Ln} |
| | $FS_{Ln/Fe}$ | $FS_{Ln/Fe}$ | $FS_{Ln/Fe}$ | $FS_{Ln/Fe}$ |
| La | <0.1 | <0.1 | <0.1 | 0.1< |
| Nd | <0.1 | <0.1 | <0.1 | 0.1< |
| Gd | <0.1 | <0.1 | <0.1 | 0.1< |
| Dy | 0.6 | 0.1 | 0.1 | 0.2 |
| Yb | 20 | 3 | 2 | 2.5 |

The calculated values of the selectivity factors FS of the element Yb compared to each element M, noted $FS_{Yb/M}$, are reported in table 8.3 below:

TABLE 8.3

| | [H$_3$PO$_4$] (in M) | | | |
|---|---|---|---|---|
| | 5 | 3 | 1 | 0.5 |
| Element M | | | | |
| | $FS_{Yb/M}$ | $FS_{Yb/M}$ | $FS_{Yb/M}$ | $FS_{Yb/M}$ |
| Fe | 20 | 3 | 2 | 2.5 |
| La | >200 | >200 | >200 | >200 |
| Nd | >200 | >200 | >200 | >200 |
| Gd | >200 | >200 | >200 | >200 |
| Dy | 35 | 23 | 18 | 12 |

The results of examples 13 to 15 show that the presence of a branching in alpha position with respect to the phosphonate group or to the amide group makes it possible to extract efficiently and selectively Yb and this for all molar concentrations of [H$_3$PO$_4$] (from 0.5 M to 5 M). It is observed, in fact, that lanthanides of atomic number lower than that of Yb (Ln=La, Nd, Gd, Dy) are not, or are little, extracted.

Extraction agents comprising a branching in alpha position with respect to the phosphonate group or to the amide group thus have interesting performances for the extraction of Yb with good selectivity with respect to Fe. By increasing the molar concentration of extraction agent to values comprised between 15 mM and 25 mM, Yb extraction performances that lie between 71% and 80% are obtained, while conserving good separation factors ($FS_{Yb/Fe}$>200), at high acidity ([H$_3$PO$_4$]=5 M).

By comparing the results of examples 13 and 14 with those of example 15, it may be observed that an extraction agent comprising a branching in alpha position with respect to the phosphonate group ($R_1$=Oct in example 13 or $R_1$=CH$_3$ in example 14) leads to improved Yb extraction performances compared to those of an extraction agent comprising a branching in alpha position with respect to the amide group ($R_2$=CH$_3$ in example 15), in particular for low molar concentrations of [H$_3$PO$_4$] (0.5 M and 1 M). An optimum efficiency/selectivity for 1 M and 3 M molar concentrations of [H$_3$PO$_4$] is notably obtained.

Furthermore, when the extraction agent comprises a branching in alpha position with the respect to the phosphonate group ($R_1 \neq$ H), it is observed that the Yb extraction performance is improved when this branching is a methyl branching ($R_1$=CH$_3$ in example 14) compared to an n-octyl branching ($R_1$=Oct in example 13).

BIBLIOGRAPHY

[1] S. Ansari et al., *Chem. Rev.*, 2012, 112, 1751-1772
[2] H. Narita et al., *Solvent Extraction Research and Development, Japan*, 2013, 20, 115-121
[3] M. Iqbal et al., New J. Chem., 2012, 36, 2048-2059

The invention claimed is:
1. A method for extracting at least one rare earth from an aqueous phase in which the at least one rare earth is present, the aqueous phase further comprising phosphoric acid, comprising:
contacting the aqueous phase with an organic phase comprising at least one compound of formula (I):

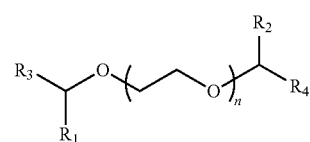

wherein n is an integer equal to 0, 1 or 2,
$R_1$ and $R_2$ are, independently of each other, a hydrogen atom, a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched,
one of $R_3$ and $R_4$ has formula (II):

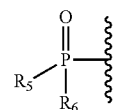

wherein $R_5$ and $R_6$ are, independently of each other, a $C_1$ to $C_{12}$ aliphatic hydrocarbon group, saturated or unsaturated, linear or branched, a $C_3$ to $C_8$ cyclic hydrocarbon group, saturated or unsaturated, optionally branched, a hydroxyl group —OH or an alkoxyl group —OR, with R being a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched, and
the other one of $R_3$ and $R_4$ has:
either formula (II'):

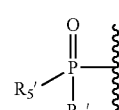

wherein $R_5'$ and $R_6'$ are, independently of each other, a $C_1$ to $C_{12}$ aliphatic hydrocarbon group, saturated or unsaturated, linear or branched, a $C_3$ to $C_8$ cyclic hydrocarbon group, saturated or unsaturated, optionally branched, a hydroxyl group —OH or an alkoxyl group —OR', with R' being a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched,
or
formula (III):

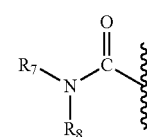

wherein $R_7$ and $R_8$ are, independently of each other, a hydrogen atom, a $C_1$ to $C_{12}$ aliphatic hydrocarbon group, saturated or unsaturated, linear or branched, or a C$_3$ to C$_8$ cyclic aliphatic hydrocarbon group, saturated or unsaturated, optionally branched and separating the aqueous phase from the organic phase.

2. The method according to claim 1, wherein the compound has formula (I-a):

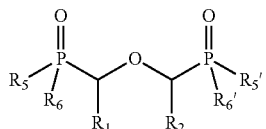

(I-a)

wherein R$_5$ and/or R$_6$ are a hydroxyl group —OH.

3. The method according to claim 2, wherein
one of R$_5$ and R$_6$ is a hydroxyl group —OH and the other one of R$_5$ and R$_6$ is an alkoxyl group —OR, with R being a C$_2$ to C$_8$ alkyl group, linear or branched, and R$_5$' and R$_6$' are, independently of each other, a C$_4$ to C$_{10}$ alkyl group, linear or branched.

4. The method according to claim 1, wherein the compound has formula (I-b):

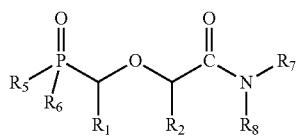

(I-b)

wherein R$_5$ and/or R$_6$ are a hydroxyl group —OH.

5. The method according to claim 4, wherein
one of R$_5$ and R$_6$ is a hydroxyl group —OH and the other one of R$_5$ and R$_6$ is a C$_4$ to C$_{10}$ alkyl group, linear or branched, or a C$_2$ to C$_8$ alkoxyl group —OR, with R being an alkyl group, linear or branched, and
R$_7$ and R$_8$ are, independently of each other, a C$_4$ to C$_{10}$ alkyl group, linear or branched.

6. The method according to claim 2, wherein R$_1$ and R$_2$ are each a hydrogen atom.

7. The method according to claim 2, wherein R$_1$ and R$_2$ are each a C$_1$ to C$_{10}$ alkyl group, linear or branched.

8. The method according to claim 2, wherein one of R$_1$ and R$_2$ is a hydrogen atom and the other one of R$_1$ and R$_2$ is a C$_1$ to C$_{10}$ alkyl group, linear or branched.

9. The method according to claim 8, wherein R$_2$ is a hydrogen atom.

10. The method according to claim 1, wherein the aqueous phase is an acid digestion solution of a concentrate of a natural or urban ore comprising the at least one rare earth.

11. The method according to claim 1, wherein the aqueous phase comprises at least 0.1 mol/L of the phosphoric acid.

12. The method according to claim 1, wherein the extraction is carried out by liquid-liquid extraction by means of an organic phase comprising at least 10$^{-3}$ mol/L of the compound in solution in an organic diluent.

13. A method for recovering at least one rare earth present in an aqueous phase, the aqueous phase further comprising phosphoric acid, the method comprising:

a) extracting the at least one rare earth from the aqueous phase by bringing the aqueous phase into contact with an organic phase comprising at least one compound of formula (I):

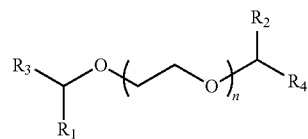

(I)

wherein n is an integer equal to 0, 1 or 2,

R$_1$ and R$_2$ are, independently of each other, a hydrogen atom, a C$_1$ to C$_{12}$ aliphatic hydrocarbon group, saturated or unsaturated, linear or branched, or a C$_3$ to C$_8$ cyclic aliphatic hydrocarbon group, saturated or unsaturated, optionally branched, one of R$_3$ and R$_4$ has formula (II):

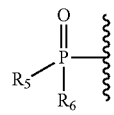

(II)

wherein R$_5$ and R$_6$ are, independently of each other, a C$_1$ to C$_{12}$ aliphatic hydrocarbon group, saturated or unsaturated, linear or branched, a C$_3$ to C$_8$ cyclic hydrocarbon group, saturated or unsaturated, optionally branched, a hydroxyl group —OH or an alkoxyl group —OR, with R being a C$_1$ to C$_{12}$ aliphatic hydrocarbon group, saturated or unsaturated, linear or branched, or a C$_3$ to C$_8$ cyclic aliphatic hydrocarbon group, saturated or unsaturated, optionally branched, and the other one of R$_3$ and R$_4$ has:
either formula (II'):

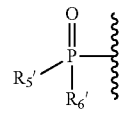

(II')

wherein R$_5$' and R$_6$' are, independently of each other, a C$_1$ to C$_{12}$ aliphatic hydrocarbon group, saturated or unsaturated, linear or branched, a C$_3$ to C$_8$ cyclic hydrocarbon group, saturated or unsaturated, optionally branched, a hydroxyl group —OH or an alkoxyl group —OR', with R' being a C$_1$ to C$_{12}$ aliphatic hydrocarbon group, saturated or unsaturated, linear or branched, or a C$_3$ to C$_8$ cyclic aliphatic hydrocarbon group, saturated or unsaturated, optionally branched, or formula (III):

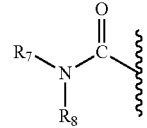

(III)

wherein R$_7$ and R$_8$ are, independently of each other, a hydrogen atom, a C$_1$ to C$_{12}$ aliphatic hydrocarbon group, saturated or unsaturated, linear or branched, or a $C_3$ to $C_8$ cyclic aliphatic hydrocarbon group, saturated or unsaturated, optionally branched, then separating the aqueous phase from the organic phase; and b) stripping the at least one rare earth present in the organic phase as obtained at the end of step a) by bringing the organic phase into contact with an aqueous phase, then separating the organic phase from the aqueous phase.

14. The method according to claim 13, wherein the aqueous phase comprising phosphoric acid is a phosphoric acid digestion solution of a concentrate of a natural or urban ore comprising the at least one rare earth.

15. The method according to claim 13, wherein, during step a) at least one salt is added to the aqueous phase.

16. The method according to claim 15, wherein a molar concentration of salt(s) is from 0.01 mol/L to 4 mol/L.

17. The method according to claim 15, wherein the at least one salt is sodium nitrate.

18. A compound of formula (I-a):

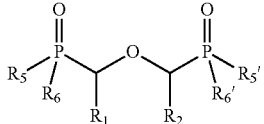

(I-a)

wherein $R_1$ and $R_2$ are, independently of each other, a hydrogen atom, a $C_1$ to $C_{12}$ aliphatic hydrocarbon group, saturated or unsaturated, linear or branched, or a $C_3$ to $C_8$ cyclic aliphatic hydrocarbon group, saturated or unsaturated, optionally branched, one of $R_5$ and $R_6$ is a hydroxyl group —OH and the other one of $R_5$ and $R_6$ is an alkoxyl group —OR, with R being a $C_2$ to $C_8$ alkyl group, linear or branched, and $R_5'$ and $R_6'$ are, independently of each other, a $C_4$ to $C_{10}$ alkyl group, linear or branched.

* * * * *

UNITED STATES PATENT AND TRADEMARK OFFICE
CERTIFICATE OF CORRECTION

PATENT NO. : 10,450,629 B2
APPLICATION NO. : 15/571967
DATED : October 22, 2019
INVENTOR(S) : Fanny Mary et al.

Page 1 of 1

It is certified that error appears in the above-identified patent and that said Letters Patent is hereby corrected as shown below:

On the Title Page

Item (72), the second inventor's city is incorrect. Item (72) should read:
-- (72) Inventors: Fanny Mary, Valreas (FR); Guilhem Arrachart, Saint-Laurent-des-Arbres (FR); Stephane Pellet-Rostaing, Villeurbanne (FR); Antoine Leydier, Saint Etienne (FR); Veronique Dubois, Gaujac (FR) --

Item (73), the first Assignee information is incorrect. Item (73) should read:
-- (73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris Cedex 16 (FR); UNIVERSITE DE MONTPELLIER, Montpellier (FR) --

Signed and Sealed this
Twenty-eighth Day of April, 2020

Andrei Iancu
*Director of the United States Patent and Trademark Office*